US012796769B2

(12) United States Patent
Chen

(10) Patent No.: US 12,796,769 B2
(45) Date of Patent: Nov. 17, 2026

(54) SYSTEM AND METHOD FOR A SMART SHOE BASED KINESIOLOGY AND PHYSIOLOGICAL DATA COLLECTION

(71) Applicant: Surplex, Co

(72) Inventor: Zijia Chen, Boston, MA (US)

(73) Assignee: Surplex, Co., Boston, MA (US)

( * ) Notice: Subject to any disclaimer, the term of this patent is extended or adjusted under 35 U.S.C. 154(b) by 0 days.

(21) Appl. No.: 19/078,725

(22) Filed: Mar. 13, 2025

(65) Prior Publication Data

US 2025/0325067 A1 Oct. 23, 2025

Related U.S. Application Data

(60) Provisional application No. 63/679,031, filed on Aug. 2, 2024, provisional application No. 63/634,988, filed on Apr. 17, 2024.

(51) Int. Cl.

| | |
|---|---|
| ***A43B 3/44*** | (2022.01) |
| ***A41B 11/00*** | (2006.01) |
| ***A61B 5/00*** | (2006.01) |
| ***A61B 5/103*** | (2006.01) |
| ***G01L 1/18*** | (2006.01) |
| ***G01L 5/162*** | (2020.01) |

(52) U.S. Cl.

CPC ................ *A43B 3/44* (2022.01); *A41B 11/00* (2013.01); *A61B 5/1038* (2013.01); *A61B 5/6807* (2013.01); *G01L 1/18* (2013.01); *G01L 5/162* (2013.01); *A61B 2562/0247* (2013.01); *A61B 2562/04* (2013.01); *A61B 2562/125* (2013.01); *A61B 2562/164* (2013.01)

(58) Field of Classification Search

CPC ................................. A43B 11/00; A43B 3/44
USPC ............................................................. 36/43
See application file for complete search history.

(56) References Cited

U.S. PATENT DOCUMENTS

| | | | | |
|---|---|---|---|---|
| 9,460,557 | B1 * | 10/2016 | Tran | G06T 17/20 |
| 11,805,850 | B1 * | 11/2023 | Dananberg | A43B 7/1425 |
| 2012/0186101 | A1 * | 7/2012 | Sanchez | A43B 7/142 36/43 |
| 2015/0068069 | A1 * | 3/2015 | Tran | G08B 21/023 340/693.1 |
| 2016/0081418 | A1 * | 3/2016 | Amos | A61B 5/6807 36/43 |
| 2016/0262485 | A1 * | 9/2016 | Walker | A43B 7/088 |
| 2022/0326099 | A1 * | 10/2022 | Chong | G01L 1/18 |
| 2023/0180893 | A1 * | 6/2023 | Mathieu | A43B 7/141 36/43 |

* cited by examiner

*Primary Examiner* — Timothy K Trieu
(74) *Attorney, Agent, or Firm* — AKC PATENTS, LLC; Aliki K. Collins

(57) ABSTRACT

A smart shoe system, includes a shoe having a shoe body, a shoe sole, and an insole. The shoe sole is attached to an outer surface of the shoe body's bottom, the insole is located within the shoe body onto an inner surface of the shoe body's bottom, and the shoe body is shaped and dimensioned to receive a user's foot. The insole includes a flexible pressure sensor array and impedance sensing electrodes. The flexible pressure sensor array includes a first electrode, a second electrode, and a flexible composite piezoresistive layer interposed between the first and second electrodes. Each of the first and second electrodes includes a flexible substrate and a flexible conductive electrode structure that is bonded to the flexible substrate.

21 Claims, 25 Drawing Sheets

123

507

504

SYSTEM AND METHOD FOR A SMART SHOE BASED KINESIOLOGY AND PHYSIOLOGICAL DATA COLLECTION

CROSS REFERENCE TO RELATED CO-PENDING APPLICATIONS

This application claims the benefit of U.S. provisional application Ser. No. 63/634,988 filed on Apr. 17, 2024 and entitled "Smart shoe system for comprehensive kinesiology and physiological data collection", which is commonly assigned and the contents of which are expressly incorporated herein by reference.

This application claims the benefit of U.S. provisional application Ser. No. 63/679,031 filed on Aug. 2, 2024 and entitled "Adaptive AI-driven smart insole system for real-time performance optimization and injury prevention", which is commonly assigned and the contents of which are expressly incorporated herein by reference.

FIELD OF THE INVENTION

The present invention relates to a system and a method for a smart shoe based kinesiological and physiological data collection, and specifically to a smart shoe designed for monitoring and analyzing human movement and physiological parameters to enhance health, and athletic performance, and to prevent injuries.

BACKGROUND OF THE INVENTION

In the realm of wearable technology, there has been a significant shift towards developing devices that not only track physical activity but also provide insights into the user's overall health and biomechanics. Despite this progress, current offerings in the market predominantly focus on singular aspects of health or performance monitoring, such as step counting, heart rate tracking, or sleep monitoring. These devices, while useful, fall short of providing a holistic view of the wearer's physiological and biomechanical status, especially in dynamic and complex physical activities.

Moreover, most existing technologies lack the precision and breadth of data collection necessary for a comprehensive analysis of human movement and its underlying physiological markers. For example, most conventional fitness trackers and smartwatches excel at tracking straightforward metrics such as steps taken and heart rate for distance runners. However, they rarely integrate these data with biomechanical analysis, such as the impact of cadence on hydration level. Similarly, devices equipped with bioelectrical impedance analysis for monitoring hydration and body composition are not designed to assess how these factors correlate with the wearer's biomechanical efficiency or athletic performance.

Another critical gap in current wearable technology is the integration of data types. Devices that do offer multiple forms of data collection often operate in silos, with little to no cross-analysis between biomechanical and physiological data points. This separation limits the utility of the data collected, as the interplay between these data types is crucial for a truly comprehensive understanding of the wearer's health and performance.

SUMMARY OF THE INVENTION

The present invention relates to a system and a method for a smart shoe based kinesiological and physiological data collection, and specifically to a smart shoe designed for monitoring and analyzing human movement and physiological parameters to enhance health, and athletic performance, and to prevent injuries.

In general, in one aspect the invention provides a smart shoe system including a shoe comprising a shoe body, a shoe sole, and an insole. The shoe sole is attached to an outer surface of the shoe body's bottom, the insole is located within the shoe body onto an inner surface of the shoe body's bottom, and the shoe body is shaped and dimensioned to receive a user's foot. The insole includes a flexible pressure sensor array, and the flexible pressure sensor array comprises an upper electrode, a lower electrode, and a flexible composite piezoresistive layer interposed between the upper and lower electrodes. Each of the upper and lower electrodes comprises a flexible substrate and a flexible conductive electrode structure that is bonded to said flexible substrate.

Implementations of this aspect of the invention include one or more of the following. The smart shoe system further comprises a computing module electrically connected to the insole. The computing module includes an inertial measurement unit, a barometer, microcontroller, and a wireless signal transmitter. The smart shoe system further includes a bioimpedance sensor system and the bioimpedance sensor system includes impedance sensing electrodes, and an impedance sensing module. The computing module further includes the impedance sensing module and is electrically connected to the impedance sensing electrodes. The smart shoe system further includes a mobile communication device configured to wirelessly connect to the computing module via the wireless signal transmitter and to receive sensor data from the flexible pressure sensor array, the impedance sensing module, the inertial measurement unit, the barometer and the microcontroller. The mobile communication device includes an application that provides real time feedback to a user during use of the shoe based on the sensor data. The sensor data are relayed to a computing cloud for advanced analysis by a computer and the smart shoe system further includes a cloud-based artificial intelligence (AI) application, which performs the advanced analysis of the sensor data by the computer. The cloud-based artificial intelligence (AI) application includes computation modules that perform the advanced analysis of the sensor data. The computation modules include a first layer of encoders that encode the sensor data, and extract first feature data from all encoded sensor data, a combinator that forms all possible combinations of the first feature data and generates combined first feature data, a second layer of encoders that encode the combined first feature data and extract second feature data, a data synthesis and analysis module that synthesizes and analyzes the first feature data and the second feature data and generates refined data, and a processor that processes the refined data and generates actionable insights into the user's physiological and biomechanical states. The layer of encoders incorporates temporal sequences to the first feature data and creates a three-dimensional feature data space. The smart shoe system further includes a conductive sock comprising conductive fibers, and the conductive sock surrounds the user's foot and is electrically connected to the computing module. The flexible composite piezoresistive layer includes an elastomer matrix impregnated with conductive particles. The conductive particles may be one of carbon black, graphene, graphene oxide, silver nanoparticles, carbon nanotubes (CNTs), copper nanoparticles, conductive polyaniline (PANI), Poly (3,4-ethylenedioxythiophene) polystyrene sulfonate (PE- DOT:PSS), two-dimensional materials made of transition metal carbides, carbonitrides and nitrides (MXenes), metal-organic frameworks (MOFs), or combinations thereof. The elastomer matrix may be one of polyethylene (PE), low-density polyethylene (LDPE), polyurethane (PU), polydimethylsiloxane (PDMS), silicone rubber (VMQ), styrene-butadiene rubber (SBR), ethylene-vinyl acetate (EVA), fluoroelastomers (FKM), natural rubber (NR), or other flexible polymeric elastomers. The flexible composite piezoresistive layer includes micro-dome elements and/or porous sections. The flexible substrate may include one of acetate, polyester, polyimide, or flexible polymer films. The flexible conductive electrode structure may be one of silver-plated fabrics, nickel/copper-plated fabric, conductive inks, or carbon-based conductive polymers. The flexible conductive electrode structure is bonded to the flexible substrate via one of fabric glue, thermal bonding, ultrasonic welding, adhesive bonding or lamination techniques. The flexible conductive electrode structure is shaped via laser cutting or high-precision die-cutting. The computing module is located within the shoe sole, or is attached to the shoe sole's bottom or is configured to be removably located onto the shoe body. The mobile communication device may be one of a mobile phone, a smart watch, a tablet, or a networked computing unit. The insole may further include a flexible printed circuit (FPC) and the flexible pressure sensor array is connected to the FPC via a conductive adhesive.

In general, in another aspect the invention provides a method for manufacturing a smart shoe, including the following. First, providing a shoe body, a shoe sole, and an insole. The shoe body is shaped and dimensioned to receive a user's foot. Next, attaching the shoe sole to an outer surface of the shoe body's bottom and placing the insole within the shoe body onto an inner surface of the shoe body's bottom. The insole comprises a flexible pressure sensor array and impedance sensing electrodes. The flexible pressure sensor array comprises an upper electrode, a lower electrode, and a flexible composite piezoresistive layer interposed between the upper and lower electrodes. Each of the upper and lower electrodes comprises a flexible substrate and a flexible conductive electrode structure that is bonded to said flexible substrate.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

The present invention relates to a system and a method for a smart shoe based kinesiological and physiological data collection, and specifically to a smart shoe designed for monitoring and analyzing human movement and physiological parameters to enhance health, and athletic performance, and to prevent injuries.

This invention provides a smart shoe system that integrates a diverse array of sensor technologies within a shoe insole and conductive socks. This system is designed to collect and analyze kinesiological and physiological data in unison, providing a level of insight into the wearer's physical condition, biomechanics, and health metrics that is currently unparalleled in the market. By doing so, it addresses the critical need for a more holistic and integrated approach to wearable health and performance monitoring.

The need for such a system is underscored by the growing demand for personal health and performance optimization tools. As individuals become more invested in their physical well-being and athletic achievements, there is a clear need for devices that can provide comprehensive, real-time data to inform training, recovery, and overall health management strategies. This invention not only meets this demand but also sets a new standard for what wearable technologies can achieve in terms of depth, accuracy, and utility of data collection and analysis.

Figure 1A:
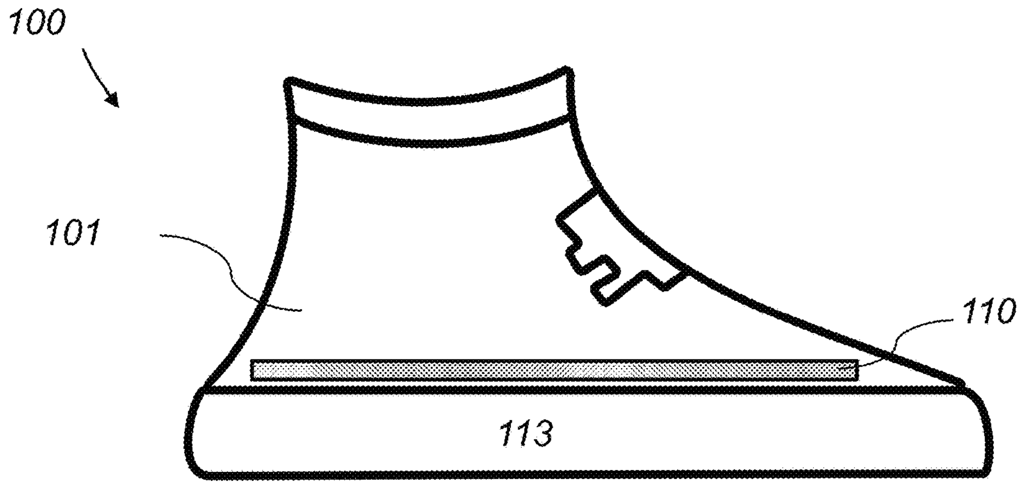
FIG. 1A depicts a schematic diagram of a smart shoe, according to this invention.
Figure 1B:
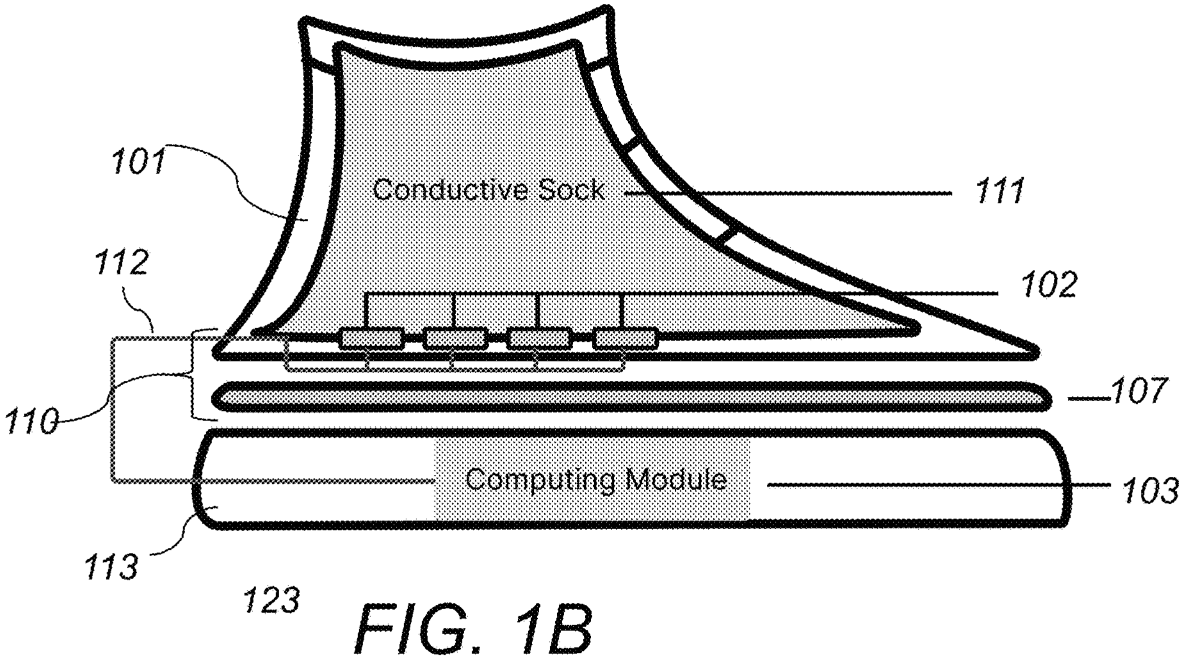
FIG. 1B depicts a cross section of the smart shoe of FIG. 1A, including the modules for detecting, identifying, and associating navigational markers in real-time, according to this invention.
Figure 1C:
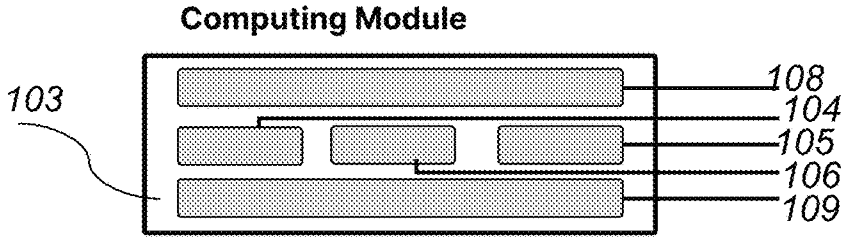
FIG. 1C depicts a schematic diagram of the computing module of the smart shoe of FIG. 1A.

The smart shoe system represents an innovative leap in wearable technology, leveraging a meticulously designed sensor array embedded within shoe insoles and conductive socks. This system is engineered to offer an unparalleled depth of analysis on an individual's biomechanical and physiological states through real-time data collection and advanced processing capabilities. Here's an expanded look at the components and operation of this system:

Referring to FIG. 1A-FIG. 1C, a smart shoe system 100 includes a shoe body 101, a shoe sole 113 arranged at the external bottom surface of the shoe body, and an insole 110 that is removably inserted onto the internal bottom surface of the shoe body 101. Insole 110 includes a textile pressure sensor array 107, and impedance sensing electrodes 102. Impedance sensing electrodes 102 are electrically connected to a computing module 103 via wires 112. A conductive sock 111 worn on the foot of a person wearing the shoe 100 is inserted into the shoe body 101 and conductively couples with the impedance sensing electrodes 102. The textile pressure sensor array 107 includes a matrix of piezoresistive sensors that are fabricated using advanced laser-cutting techniques, as will be described below. Computing module 103 includes a microcontroller with Bluetooth 108, an impedance sensing module 104, a 9-axis Inertial Measurement Unit (IMU) 105, a barometer 106, and a lithium battery 109. For bioimpedance measurements, the smart shoe system 100 utilizes the conductive sock 111 that is conductively coupled with the impedance sensing electrodes 102, and works in conjunction with the impedance sensing module 104 of the computing module 103 to measure the bioimpedance on the bottom of the foot of the shoe wearer. Movement of the shoe wearer is tracked by the 9-axis IMU 105, while elevation changes are monitored via the high-precision barometer 106. All data are processed in real-time by the computing module 103, which contains the microcontroller 108 with Bluetooth for wireless communication and is powered by the lithium battery 109. Wires 112 provide the necessary electrical connections between the impedance sensing electrodes 102 and the computing module 103. This configuration provides a comprehensive system for monitoring and analyzing physiological and biomechanical data, as further detailed in the subsequent sections.

Figure 2A:
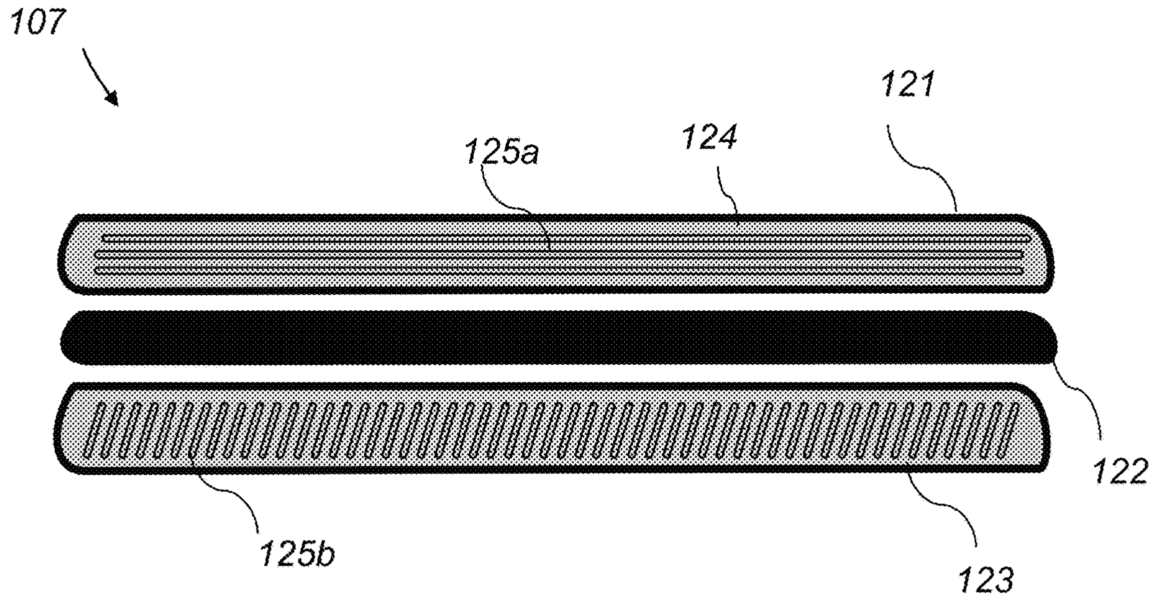
FIG. 2A depicts a cross-sectional diagram of the pressure sensor of the smart shoe of FIG. 1A.
Figure 2B:
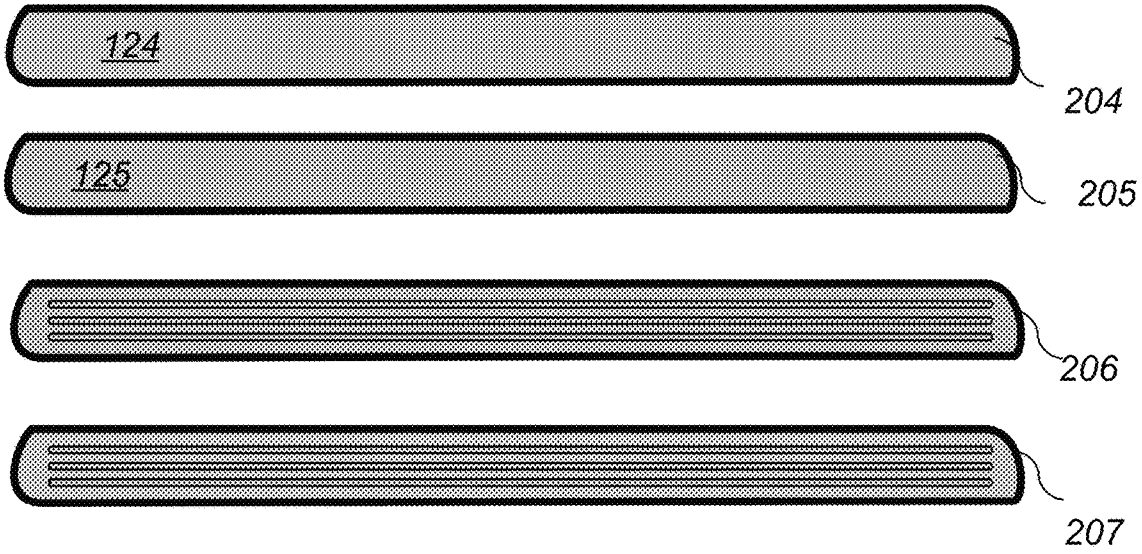
FIG. 2B depicts cross-sectional diagrams of the electrode in the pressure sensor of FIG. 2A at various manufacturing steps.

Referring to FIG. 2A, textile pressure sensor array 107 includes upper level electrodes 121, lower level electrodes 123 and a piezoresistive layer 122 sandwiched between the upper level electrodes 121 and the lower level electrodes 123. Upper level electrodes 121, and lower level electrodes 123 are critical for capturing biomechanical pressures exerted by the shoe-wearer's movements. Upper level electrodes 121, and lower level electrodes 123 are fabricated through a series of manufacturing steps 204-208, as shown in FIG. 2B. These steps 204-208 involve the preparation and processing of materials to construct the electrodes 121, 123 that form the foundation of the pressure sensor array 107 of the insole 110.

Figure 2C:
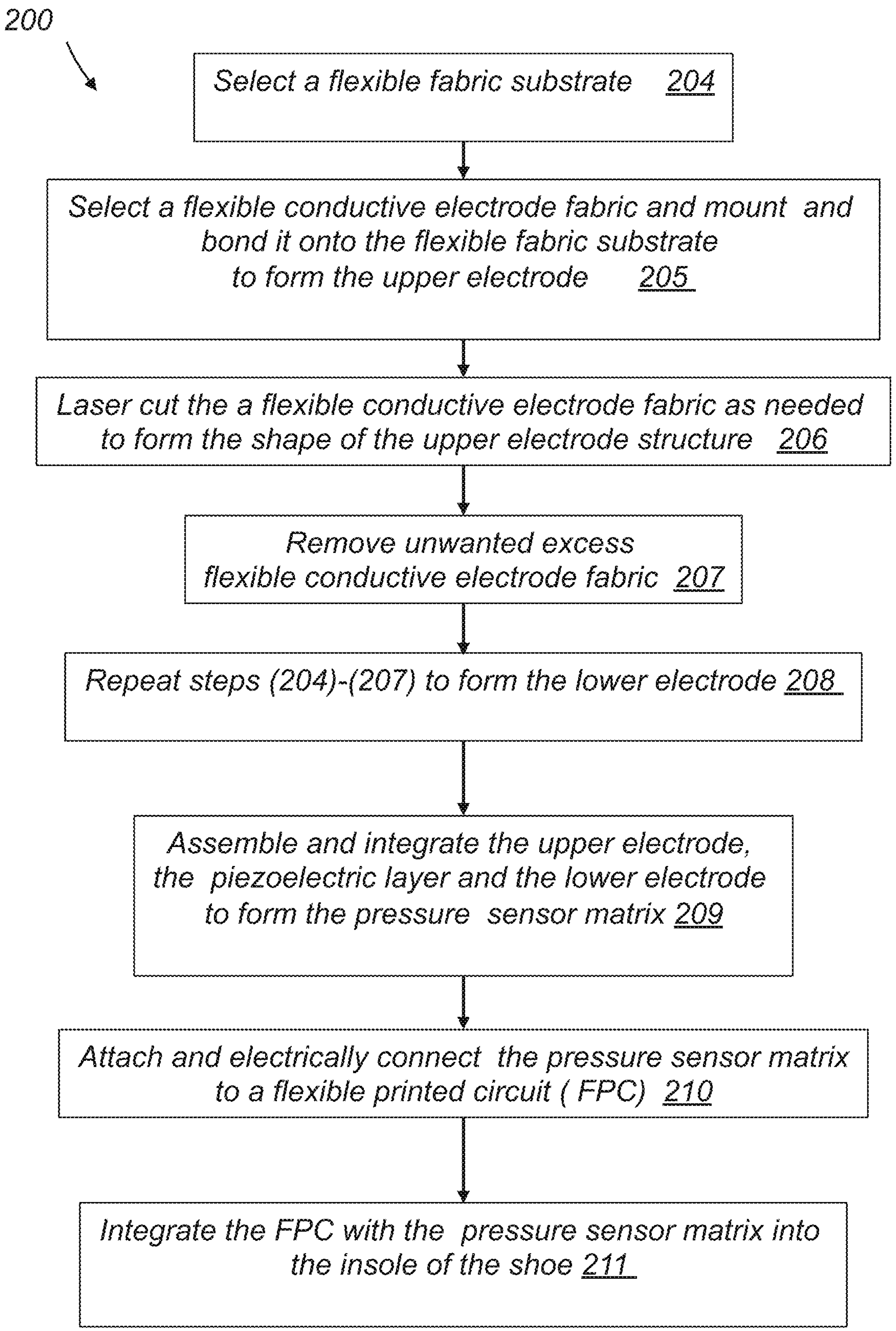
FIG. 2C is process flow diagram for manufacturing the pressure sensor of FIG. 2A.

The manufacturing process 200 for the textile pressure sensor array 107 is shown schematically in FIG. 2C. Process 200 ensures that the upper electrodes 121, and the lower electrodes 123 are optimally designed to interact with the piezoresistive material 122 placed between them, which is crucial for the sensor's ability to measure and analyze pressure changes accurately. Process 200 includes the following steps. First, a flexible fabric substrate 124 is selected (204). In one example, flexible fabric substrate 124 is a 10-mil (0.254 mm) acetate substrate. In other examples, flexible fabric substrate 124 is any suitable synthetic fabric known for its resilience and stretchability. Examples of other flexible fabric substrates 124 include polyester, polyimide, and flexible polymer films, among others. The material of the flexible fabric substrate 124 is crucial for maintaining the structural integrity and flexibility required to conform to the shoe insole's dynamic environment. Next, the upper and lower electrodes 121, 123 are formed using steps (205)-(208). Electrodes made from silver-plated fabric 125 are selected for their superior electrical conductivity and mechanical flexibility and are mounted and laminated/bonded onto the flexible fabric substrate 124 (205). In other examples, the electrodes are made of nickel/copper-plated fabric, conductive inks, metal alloys, or carbon-based conductive polymers, among others. The carbon-based conductive polymers are made of polymers impregnated with conductive particles. The polymers may be one of polyethylene (PE), polyurethane (PU), polydimethylsiloxane (PDMS), silicone rubber (VMQ), styrene-butadiene rubber (SBR), ethylene-vinyl acetate (EVA), fluoroelastomers (FKM), natural rubber (NR), or other flexible polymeric elastomers, among others. The conductive particles are made of one of carbon black, graphene, graphene oxide, silver nanoparticles, carbon nanotubes (CNTs), copper nanoparticles, conductive polyaniline (PANI), Poly(3,4-ethylenedioxythiophene) polystyrene sulfonate (PEDOT:PSS), two-dimensional materials made of transition metal carbides, carbonitrides and nitrides (MXenes), or metal-organic frameworks (MOFs), among others. The flexible fabric substrate 124 may be acetate, polyester, polyimide, flexible polymer films, cotton, acrylic, rayon, wool, or mixtures thereof, among others. The electrode lamination/bonding onto the flexible fabric substrate occurs via fabric glue, thermal bonding, ultrasonic welding, adhesive bonding or lamination techniques, among others. In one example, an acrylic-based pressure-sensitive adhesive (PSA) with a bonding strength of approximately 1.2-1.5 $N/mm^2$ is used to laminate a 10-mil (0.254 mm) acetate substrate with a nickel-copper plated conductive fabric. This adhesive ensures robust attachment while maintaining flexibility, preventing delamination under repeated mechanical stress. After the bonding step (205), each of the bonded electrodes is precisely shaped using laser cutting technology to form a high density matrix while the flexible fabric substrate remains intact (206). In one example, upper electrodes 121 are laser cut to generate a row electrode structure 125*a*, shown in FIG. 2A and FIG. 3B, and lower electrodes 123 are laser cut to generate a column electrode structure 125*b*, shown in FIG. 2B and FIG. 3A. In another example, the conductive layer 125 is selectively patterned using a $CO_2$ laser with a positional accuracy of ±0.03 mm and a cutting precision of ±50 μm, and subsequently unwanted electrode regions are selectively removed to create a well-defined row or column matrix for signal routing. In other examples, upper electrodes 121, and lower electrodes 123 are made of other conductive flexible materials including silver-plated fabrics, conductive inks, and carbon-based conductive polymers, among other. Post laser-cutting of the electrodes, excess conductive electrode fabric material is carefully removed to refine the electrode design, enhancing the precision of the active sensor areas and eliminating electrical crosstalk between adjacent electrodes (207). As an alternative to laser cutting, a high-precision die-cutting process can be employed. In this method, the conductive fabric 125 is placed into a mold with predefined cutting edges that correspond to the intended electrode layout. Using a pressure-controlled mechanical punch or rotary die cutter with a cutting tolerance of ±30 μm, excess conductive material is precisely removed, ensuring clean, well-defined electrode structures without damaging the underlying acetate substrate. This die-cutting approach enables high repeatability and uniformity while preserving the mechanical integrity and conductivity of the patterned layer, making it suitable for scalable manufacturing. Process steps (204)-(207) are repeated to form the lower electrode 123 (208). Next, the piezoresistive layer 122 is inserted and aligned between the upper electrode 121 and the lower electrode 123 and they are bonded together to form the pressure sensor matrix 107 (209). In one example, upper electrodes 121 are arranged relative to the lower electrodes 123, so that rows 125*a* intersect vertically with columns 125*b* and they form a cross-matrix that covers the entire surface of the piezoresistive layer 122. The careful alignment and bonding of the upper and lower electrodes 121, 123 with the piezoresistive layer 122 sandwiched in between, ensures consistent performance across the entire sensor area. The piezoresistive layer 122 is a composite made from an elastomer matrix impregnated with conductive particles. In one example, the elastomer matrix is made of polyethylene (PE) and the conductive particles are made of carbon black. In one specific example, an elastomer matrix composed of low-density polyethylene (LDPE) (20-30 wt. %), carbon black (5-10 wt. %), and multi-walled carbon nanotubes (MWCNTs) (1-5 wt. %) is ultrasonically homogenized at 20 kHz, 500 W for 30-60 minutes to ensure uniform dispersion of conductive fillers within the polymer matrix. This mixture is then film-extruded at 190-210° C. through a slot-die extrusion process, forming a thin film with a standard thickness of 4.0 mil (0.102 mm), though variations of 6.0 mil (0.152 mm) and 8.0 mil (0.203 mm) can be used depending on the target sensor sensitivity and mechanical properties. In other examples, the elastomer matrix may be one of polyurethane (PU), polydimethylsiloxane (PDMS), silicone rubber (VMQ), styrene-butadiene rubber (SBR), ethylene-vinyl acetate (EVA), fluoroelastomers (FKM), natural rubber (NR), or other flexible polymeric elastomers, among others. In other examples, the conductive particles are made of one of graphene, graphene oxide, silver nanoparticles, carbon nanotubes (CNTs), copper nanoparticles, conductive polyaniline (PANI), Poly(3,4-ethylenedioxythiophene) polystyrene sulfonate (PEDOT:PSS), two-dimensional materials made of transition metal carbides, carbonitrides and nitrides (MXenes), or metal-organic frameworks (MOFs), among others. In one specific example, a polyurethane (PU)-based conductive filament is developed by combining PU (85-90 wt. %), carbon black (5-10 wt. %), and MWCNTs (1-5 wt. %). This composite is first ultrasonically homogenized (20 kHz, 500 W) and then extruded into a 1.75 mm diameter filament using a twin-screw extruder at 200-220° C., ensuring uniform filler dispersion and mechanical consistency. The filament is subsequently 3D-printed using a 0.4 mm nozzle at 220-250° C., producing structured sensing layers that feature both micro-dome elements 132 (~2 mm×2 mm per dome), shown in FIG. 3H and FIG. 3J, to enhance localized stress concentration and signal output, and porous sections 134 (~100 mesh, ~147 μm pore size), shown in FIG. 3I and FIG. K, to improve compliance and pressure distribution. The micro-dome structures 132 optimize sensitivity, while the porous design 134 enhances mechanical flexibility and durability under repeated high-pressure conditions, making the sensor well-suited for dynamic applications such as running and jumping. The piezoresistive layer 122 is the key functional element of the sensor, with its resistance varying in response to pressure changes. This resistance variability as a function of the applied pressure allows the smart shoe system 100 to detect and quantify detailed variations in foot pressure during movement, essential for analyzing biomechanical efficiency. The pressure sensor matrix 107 is then electrically connected to a flexible printed circuit (FPC) (210). In one example, the sensor matrix 107 is connected to the FPC using a conductive adhesive. The FPC is constructed from a polyimide (PI) substrate and includes conductive copper traces. The conductive flexible fabric substrate 124 of the sensor matrix 107 is composed of silver-plated fabric and is electrically interfaced with the copper traces of the FPC via the conductive adhesive. The conductive adhesive may be an epoxy-based conductive adhesive or a conductive pressure-sensitive adhesive (PSA) tape embedded with metallic or carbon-based conductive particles. The FPC serves as the interface to a computing module for signal transmission and processing. This connection method provides a stable, low-resistance electrical pathway while ensuring mechanical flexibility, allowing the system to withstand repeated bending and flexing without significant degradation in electrical performance. Finally the FPC with the pressure sensor matrix 107 is integrated into the insole 110 of the smart shoe 100 (211). The integrated pressure sensor matrix 107 operates as a critical biomechanical data collection tool and provides extensive insights into the wearer's gait, contributing valuable data for applications ranging from sports science to clinical diagnostics. In one example, the biomechanical data include one or more of the following pressure distribution at the bottom of the user's feet, ground reaction forces, center of pressure trajectory, foot strike pattern, pronation and supination tendencies, step symmetry, and load distribution over time, among others.

Figure 3A:
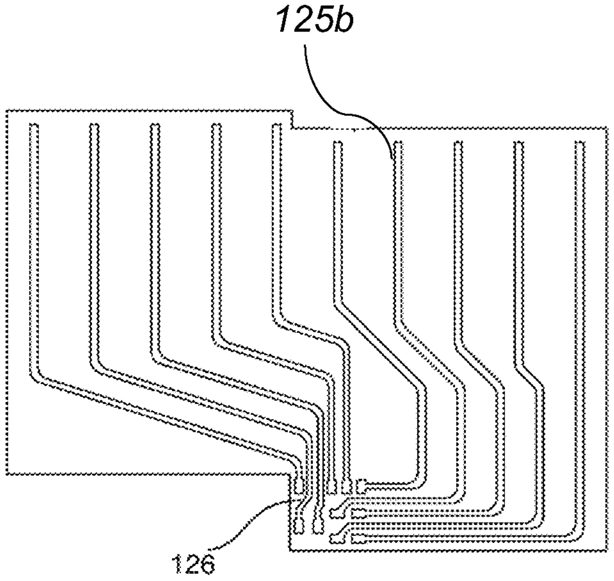
FIG. 3A depicts an image of a column electrode used in the pressure sensor of FIG. 2A.
Figure 3B:
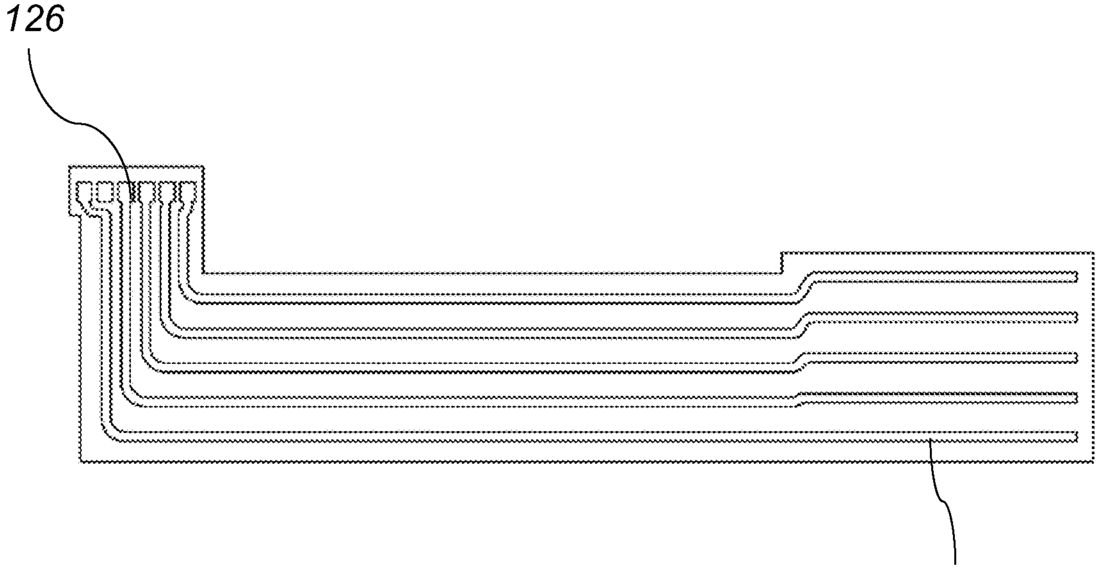
FIG. 3B depicts an image of a row electrode used in the pressure sensor of FIG. 2A.
Figure 3C:
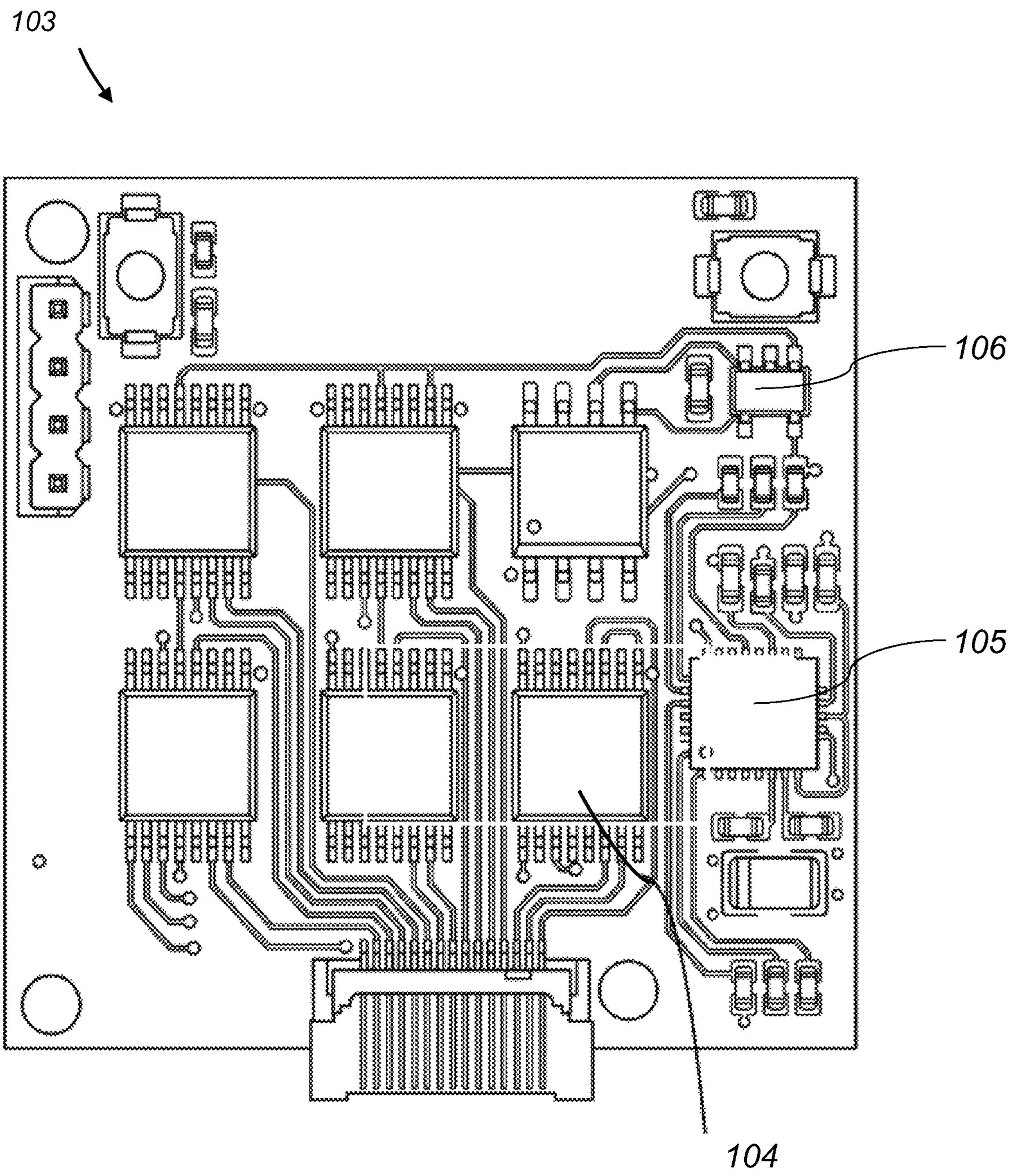
FIG. 3C depicts an image of a computing module used in the smart shoe of FIG. 1A.
Figure 3D:
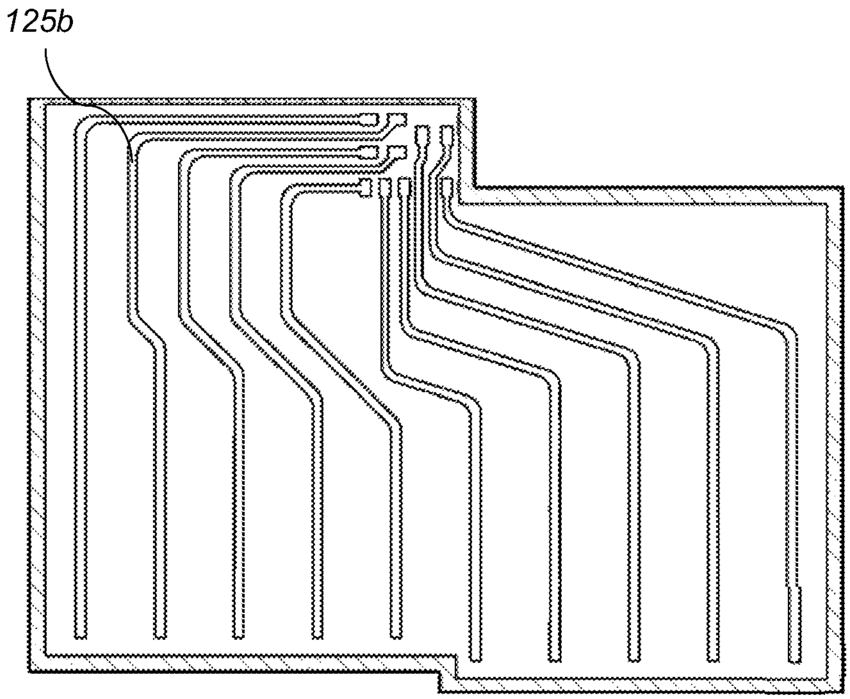
FIG. 3D depicts an image of the flexible substrate with the bonded column electrode used in the pressure sensor of FIG. 2A.
Figure 3E:
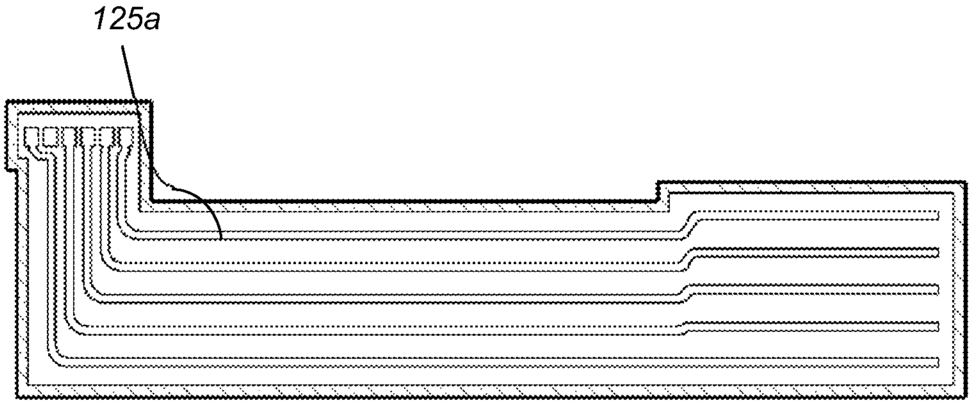
FIG. 3E depicts an image of the flexible substrate with the row electrode used in the pressure sensor of FIG. 2A.
Figure 3F:
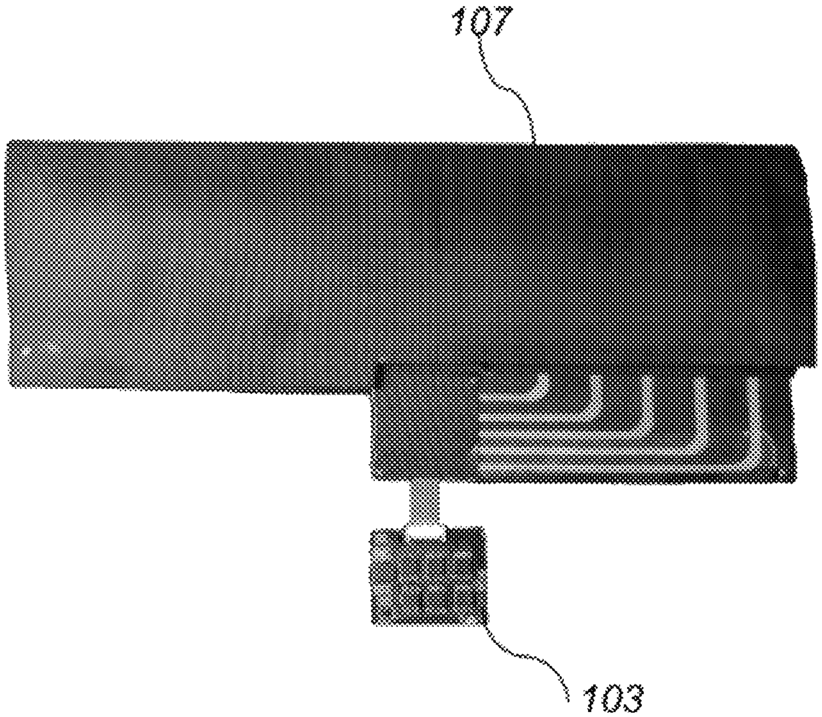
FIG. 3F depicts an image of the assembled flexible insole with the integrated pressure sensor of FIG. 2A and the computing module of FIG. 3C.
Figure 3G:
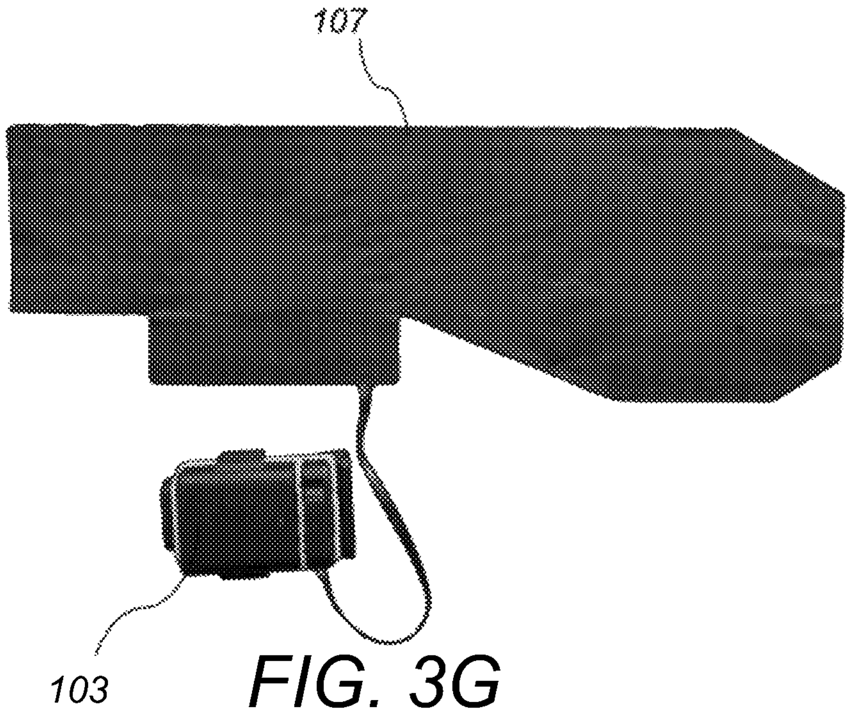
FIG. 3G depicts an image of a fully assembled flexible insole with the integrated pressure sensor of FIG. 2A and the computing module of FIG. 3C.
Figure 3H:
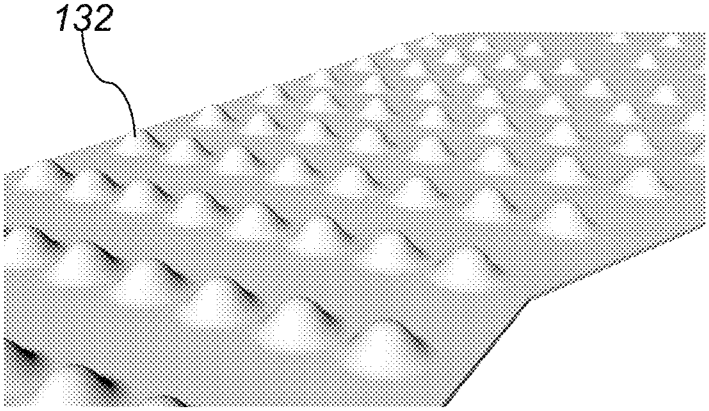
FIG. 3H depicts schematically a micro-dome structure of the piezoresistive layer of the sensor of FIG. 2A.
Figure 3I:
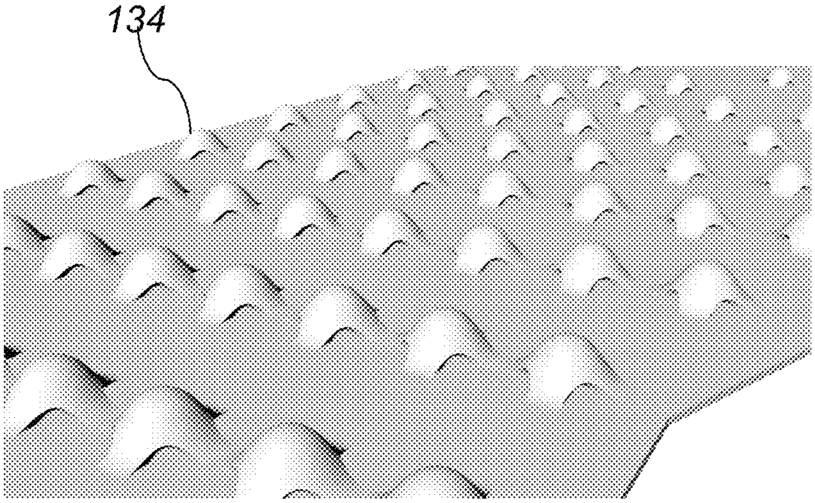
FIG. 3I depicts schematically a porous structure of the piezoresistive layer of the sensor of FIG. 2A.
Figure 3J:
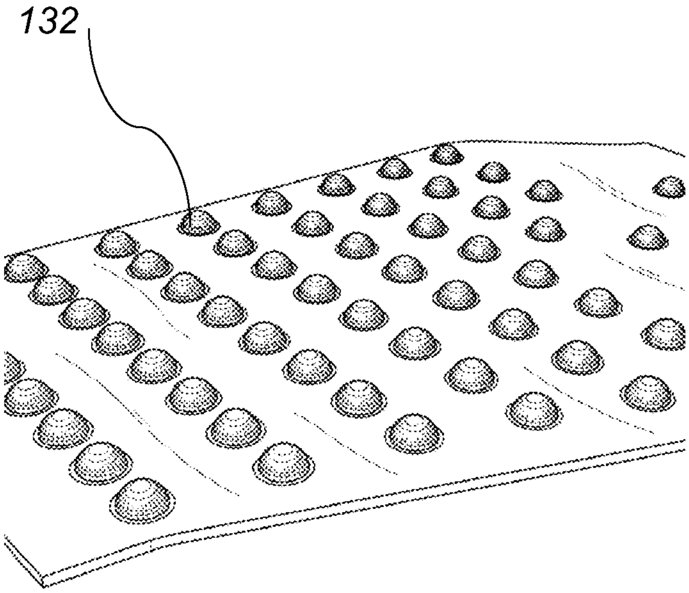
FIG. 3J depicts an actual image of the micro-dome structure of the piezoresistive layer of the sensor of FIG. 2A.
Figure 3K:
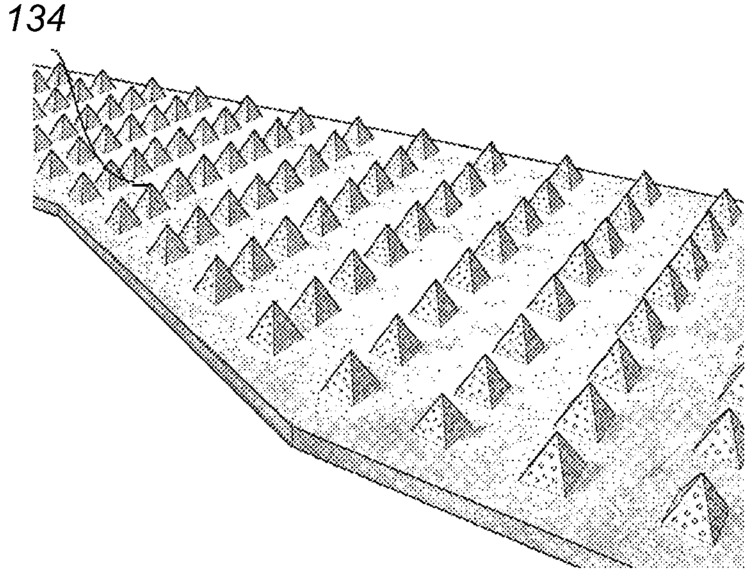
FIG. 3K depicts an actual image of the porous structure of the piezoresistive layer of the sensor of FIG. 2A.

FIG. 3A-FIG. 3K depict an example of the manufacturing process of textile pressure sensors 107 and their connection to the computing module 103. FIG. 3A depicts the laser-cut column electrode arrays 125*b* after laser cutting and before the removal of excess material, detailing the preparation for connectivity to the computing module. It features precision cut electrodes 125*b* aligned parallel with terminations 126 congregating at a specific area, thereby facilitating direct connection to the computing module 103. FIG. 3B depicts the laser-cut row electrodes 125*a* in a similar stage as in FIG. 3A. FIG. 3C displays the computing module 103 which encompasses the integrated components necessary for sensor signal processing and data transmission, including impedance sensors 104, IMU 105, barometer 106, and Bluetooth circuit for wireless data transmission. FIG. 3D and FIG. 3E depict finalized laser-cut column and row electrodes 125*b*, 125*a*, respectively, with excess material removed, ready for assembly into the sensor matrix 107. FIG. 3F and FIG. 3G depict the integration of the pressure sensor matrix 107 with the computing module 103, emphasizing the flexibility of the interface and low-profile design suitable for integration within the shoe insole 110.

The 9-Axis Inertial Measurement Unit (IMU) 105 is a composite sensor that includes accelerometers, gyroscopes, and magnetometers to track acceleration, orientation, and magnetic fields, respectively. IMU 105 provides motion related data to the system, including acceleration, distance, velocity, angular velocity, orientation, and impact forces, among others. In one example, the 9-Axis IMU is BNO085 device manufactured by Ceva, Inc. This integration offers a comprehensive view of the wearer's motion, and the obtained IMU data are used to generate a nuanced analysis of gait, running mechanics, and biomechanical efficiency. When the IMU data are analyzed in conjunction with the data from the pressure sensors, they provide an unparalleled depth of motion analysis, capturing every facet of the wearer's movement.

Barometer 106 is a high-precision centimeter-level barometer that measures pressure in centimeters of mercury (cmHg) and provides elevation data to the system. Utilizing the high-precision barometer 106, the system can detect minute elevation changes with centimeter-level accuracy. In one example, the Barometer is BMP390 device manufactured by Bosch Sensortec GmbH. This capability is paramount for understanding the vertical dynamics of activities such as jumping or running. When combined with acceleration data from the IMU 105, it provides detailed insights into the biomechanics of movement, including the impact of elevation changes on energy expenditure and joint stress.

The bioimpedance sensor system showcases a pioneering design, encompassing a bioimpedance signal conditioning module 104, impedance sensing electrodes 102, and conductive socks 111, which may be crafted from a variety of conductive threads, including but not limited to silver, stainless steel, or other conductive fibers. This flexible approach allows for the optimization of the conductive socks 111 based on specific application needs or user comfort, without compromising the system's functionality. The primary role of these conductive socks 111 is to establish a consistent and high-quality electrical pathway for a small, safe electrical current dispatched by the bioimpedance signal conditioning module 104, which flows directly through bioimpedance electrodes 102 on the insoles 110 to the user's body. Alternatively, the bioimpedance sensing can be effectively performed directly through impedance sensing electrodes 102 integrated on top of the insole 110, allowing users the convenience of opting out of the conductive socks 111, if preferred. This dual approach ensures that users have the flexibility to choose their comfort level while still benefiting from accurate physiological monitoring. The current flows into the wearer's feet and through the body's tissues, encountering varying levels of impedance reflective of different physiological states. The module's analog circuitry captures and analyzes these impedance signals, enabling the precise quantification of critical health metrics such as hydration status, body composition (detailing fat and muscle mass percentages), and certain cardiovascular health indicators. In one example, the analog circuitry is composed of AD8233 and AD5940 manufactured by Analog Devices, Inc. This system's innovative integration of adaptable conductive materials with the bioimpedance analysis technique exemplifies a cutting-edge approach to non-invasive, accurate, and real-time physiological monitoring. The bioimpedance sensor system collects physiological data through the conductive socks 111 and/or the bioimpedance electrodes 102. In one example, the physiological data include one or more of hydration levels, tissue composition, blood flow, sweat rate, muscle fatigue, or electrolyte balance, among others.

Figure 10A:
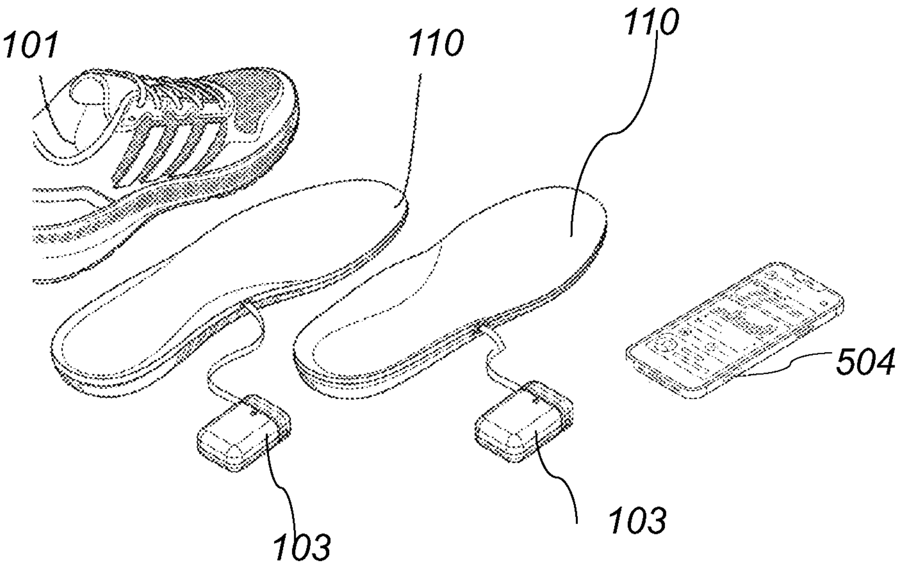
FIG. 10A depicts another embodiment of a fully assembled flexible insole with the integrated pressure sensor of FIG. 2A and the computing module of FIG. 3C, according to this invention.
Figure 10B:
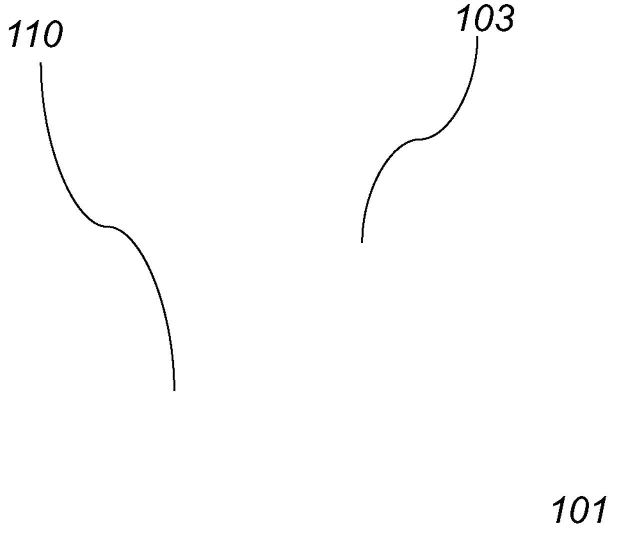
FIG. 10B depicts the flexible insole of FIG. 10A inserted into a shoe.
Figure 10C:
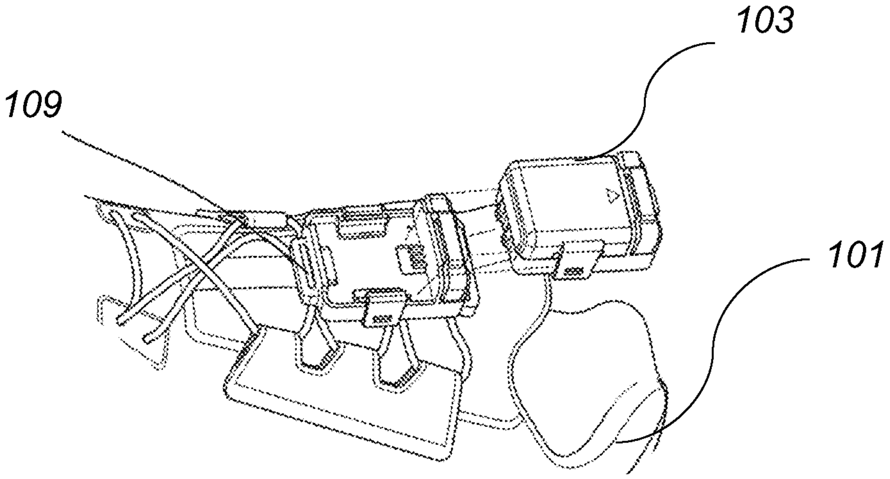
FIG. 10C depicts a removable lithium battery that powers the computing module of the insole of FIG. 10A.
Figure 10D:
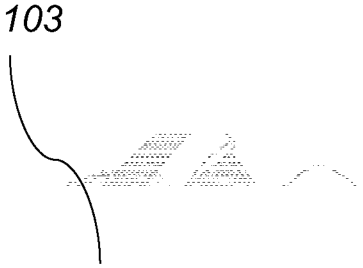
FIG. 10D depicts the computing module of the insole of FIG. 10A attached on top of a shoe.

Referring to FIG. 10A-FIG. 10D, in another embodiment insole 110 is inserted into the shoe 101 and computing module 103 is placed on top of the shoe. In this way any shoe 101 can become a smart shoe system. FIG. 10C depicts the removable lithium battery 109 that powers the computing module 103.

Figure 4:
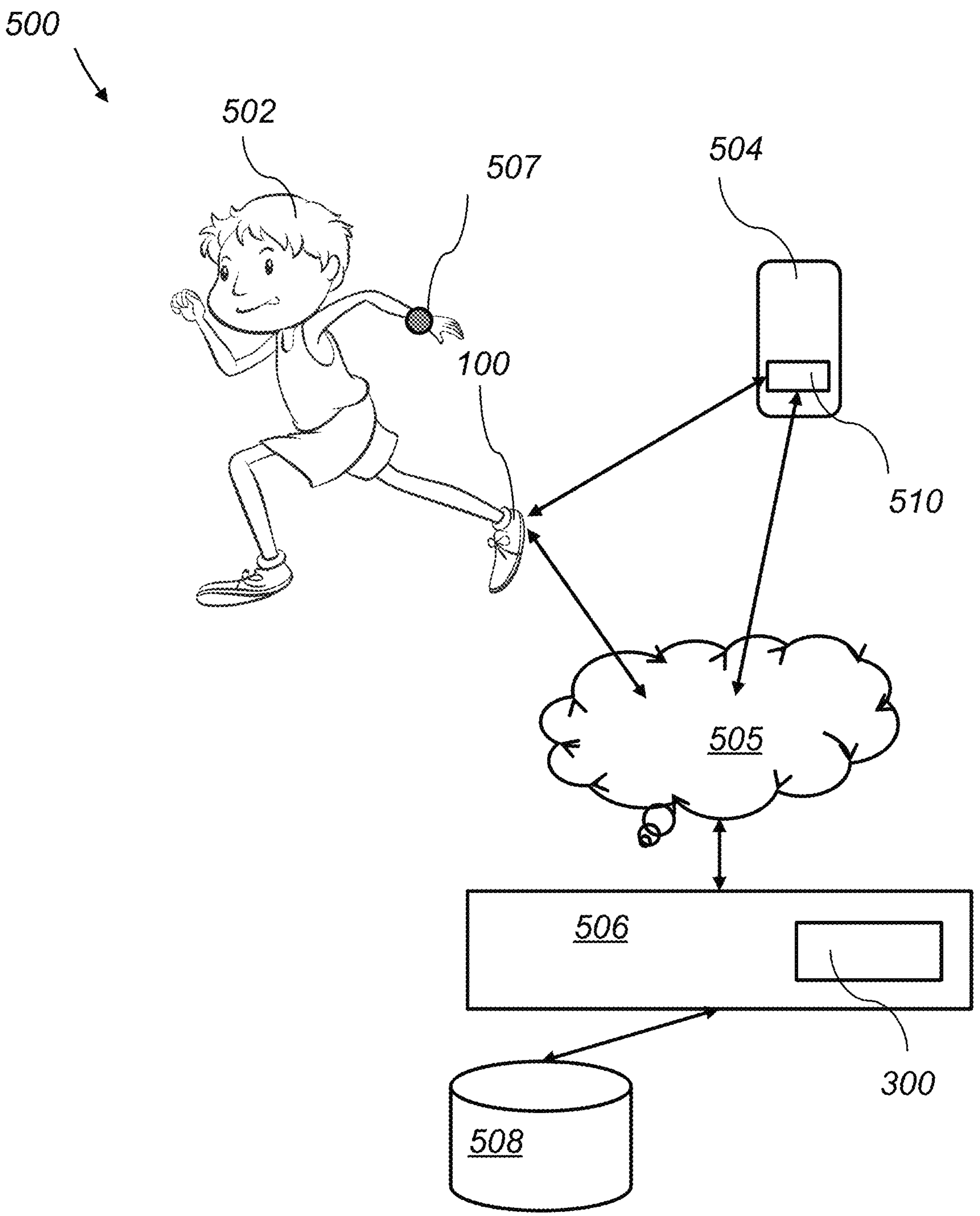
FIG. 4 depicts an overview diagram of the smart shoe system of FIG. 1B in use with an artificial intelligence (AI) application, according to this invention

Referring to FIG. 4, smart shoe system 100 is used to collect real time data from user 502 during a run. Upon activation, the smart shoe system 100 initiates immediate data collection from the integrated sensors 104, 105, 106 and 107. The data are processed on-the-fly and dispatched to the user's phone 504 via Bluetooth® and/or the user's watch 507. Simultaneously, the data are relayed to the cloud 505 for advanced analysis by computer 506. Instantaneous feedback is delivered to the user 502 through a dedicated application 510 on the user's phone 504, enabling the user to make real-time adjustments during activities such as workouts or sports events.

Figure 5A:
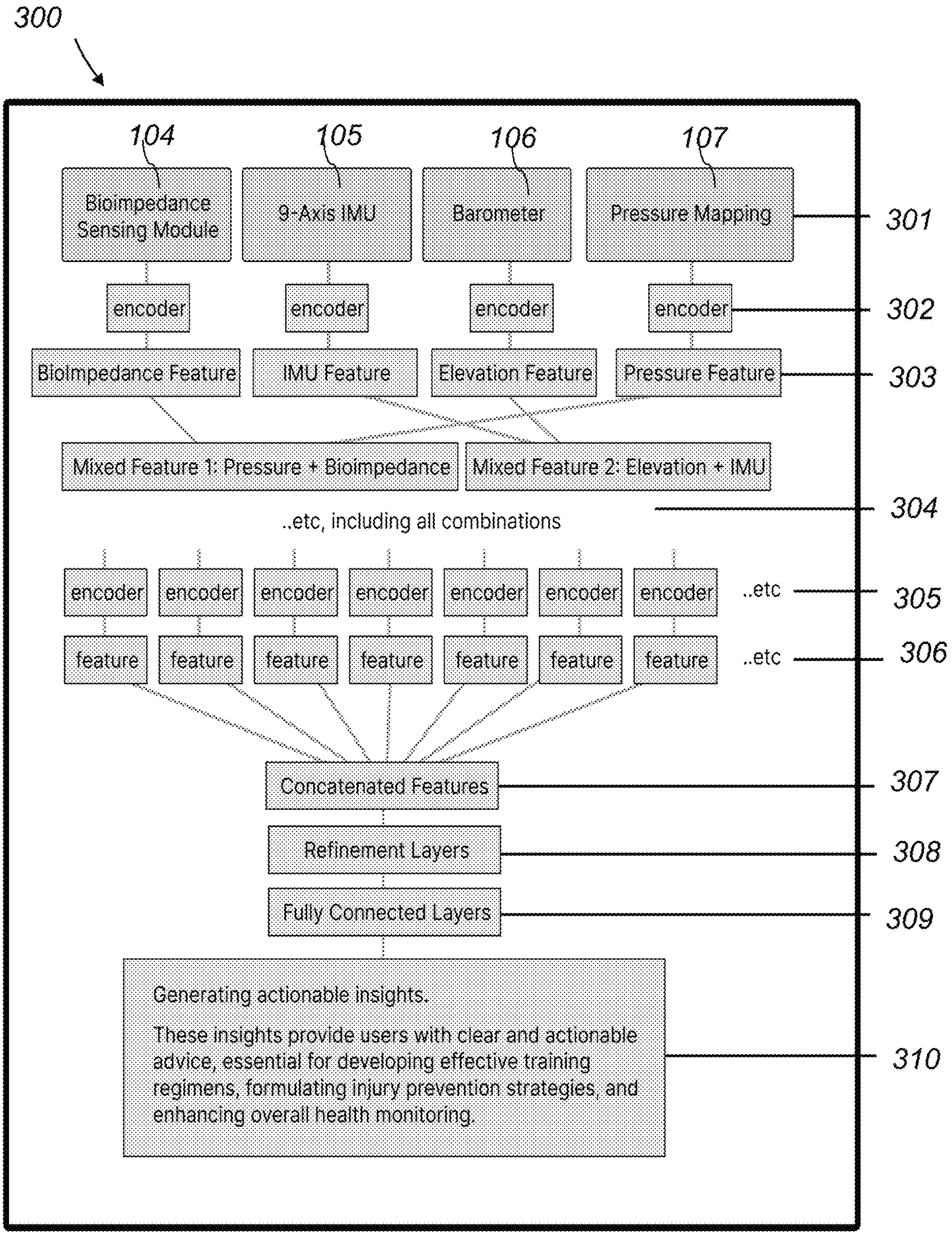
FIG. 5A depicts a block diagram of the multi-modal AI comprehension application of FIG. 4.
Figure 5B:
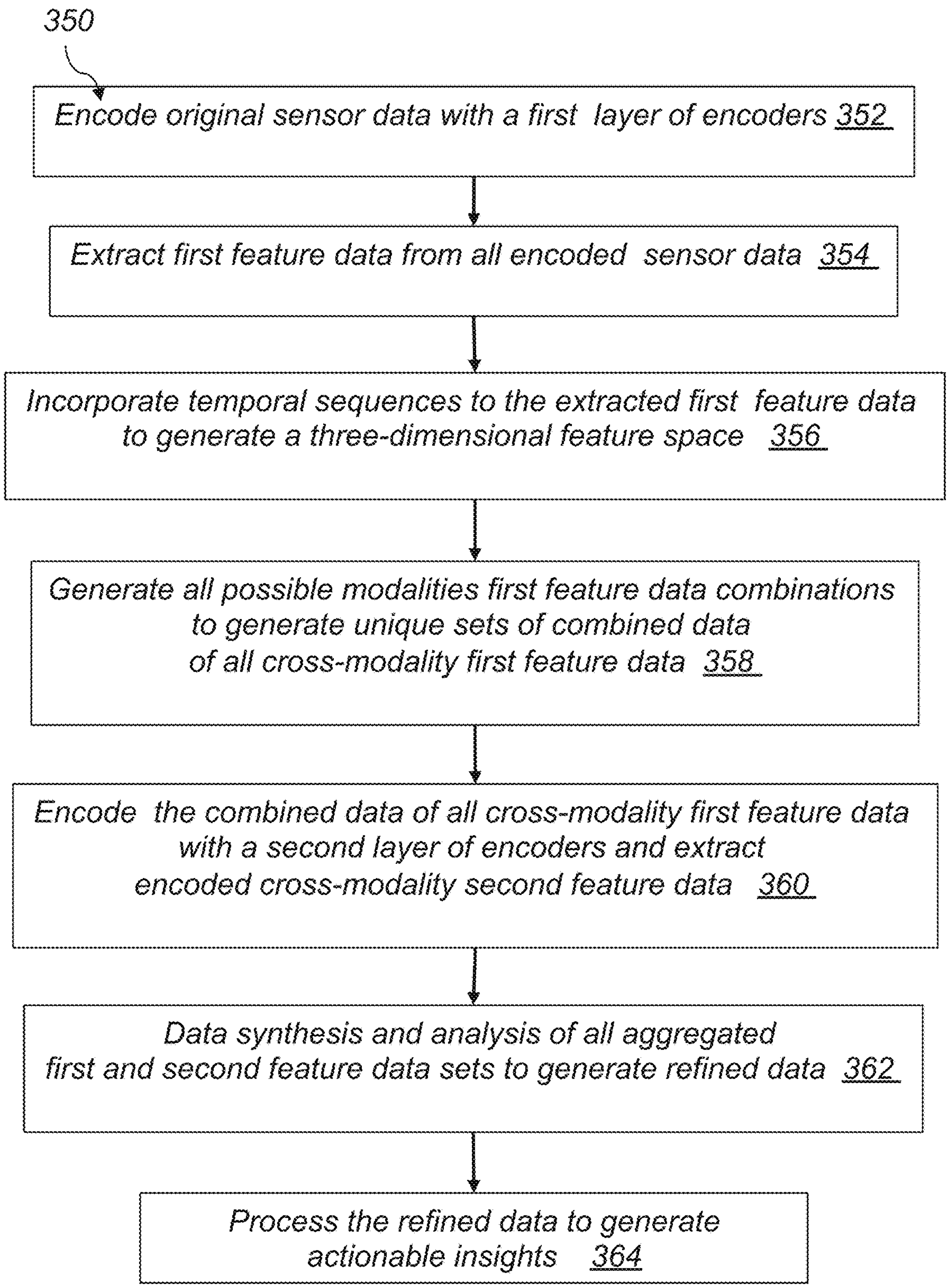
FIG. 5B is a flow diagram for the data processing and analysis provided by the AI application of FIG. 5A.

Referring to FIG. 5A and FIG. 5B, the core intelligence of the smart shoe system 100 lies in its sophisticated cloud-based artificial intelligence (AI) application 300, which performs deep analysis on the aggregated data from multiple sensors 301 including pressure sensors 107, IMU 105, barometer 106, and bioimpedance sensors 104. Application 300 includes computing modules 302, 305, 305, 307, 308, 309, 310 that implement a multi-modal AI model that utilizes advanced encoding techniques to handle and interpret a complex web of biomechanical and physiological data. The data processing and analysis methodology 350 includes the following steps. First, the original sensor data from each individual sensor modality 301 are collected and processed through specialized first encoder layers 302 (352). The encoders of the first encoder layers 302 extract first feature data from all modality sensor data 301 (354) and incorporate temporal sequences to create a three-dimensional feature space 303 (356). For instance, pressure data is transformed into a sequence of 2D images over time, while simpler sensor data like that from the barometer is expanded across the temporal dimension. Next, a combinator module 304 performs all possible combinations of the first feature data of all sensor modalities and generates combined first feature data of all possible modality combinations (358). The AI model systematically explores all possible combinations of these modalities, and forms unique sets of combined data 304. Examples of modality data combinations include the following, among others:

Pressure+IMU for detailed movement analysis;

IMU+Bioimpedance for correlating muscle activity with physiological changes;

Pressure+Elevation for understanding impact dynamics;

IMU+Elevation for advanced spatial orientation insights;

Pressure+Bioimpedance for foot health and hydration tracking;

Comprehensive combinations like Pressure+IMU+Bioimpedance+Elevation for full-spectrum analysis.

Next, a second layer of encoders 305 performs a second feature extraction (360). In this step, each first feature data modality combination undergoes further processing through the second layer of encoders 305 that are designed to extract deeper second feature data 306, thereby enhancing the model's ability to identify nuanced patterns and interactions between different types of data. The second layer of encoders 305 typically include linear or convolutional encoder layers, and are enhanced by maximum pooling layers or activation layers to refine the second feature extraction. Additional encoder layers such as recurrent neural layers for capturing dynamic temporal patterns, or attention mechanisms that prioritize significant features, are also employed to increase the model's analytical depth and accuracy. In one exemplary embodiment, the system further supports the integration of a large language model (LLM). In this configuration, the extracted feature data—whether from the first encoder layers, the combinator module, or the second encoder layers—can be interfaced with an LLM. This connection enables the LLM to perform context-aware interpretations of complex sensor data, translating the multidimensional feature representations into natural language explanations and actionable feedback. By leveraging the advanced contextual analysis capabilities of the LLM, the system can provide users with detailed, plain-language insights and personalized recommendations based on any layer of input, thereby enhancing both interpretability and user engagement.

Next, a processing module performs data synthesis and analysis of all aggregated first and second feature data to generate refined data (362). In this step, techniques such as convolution layers, pooling, and attention mechanisms are applied to refine and compress the data feature sets, and to generate concatenated features 307, refinement layers 308, and fully connected layers 309, thereby ensuring the data are both manageable and focused on the most informative aspects. The refined data are then processed to generate actionable insights 310 into the user's physiological and biomechanical states, utilizing fully connected layers to map these features directly to practical outcomes (364). These actionable insights 310 inform effective training regimens, injury prevention strategies, and health monitoring approaches, translating complex data into clear, actionable advice for users.

Figure 11A:
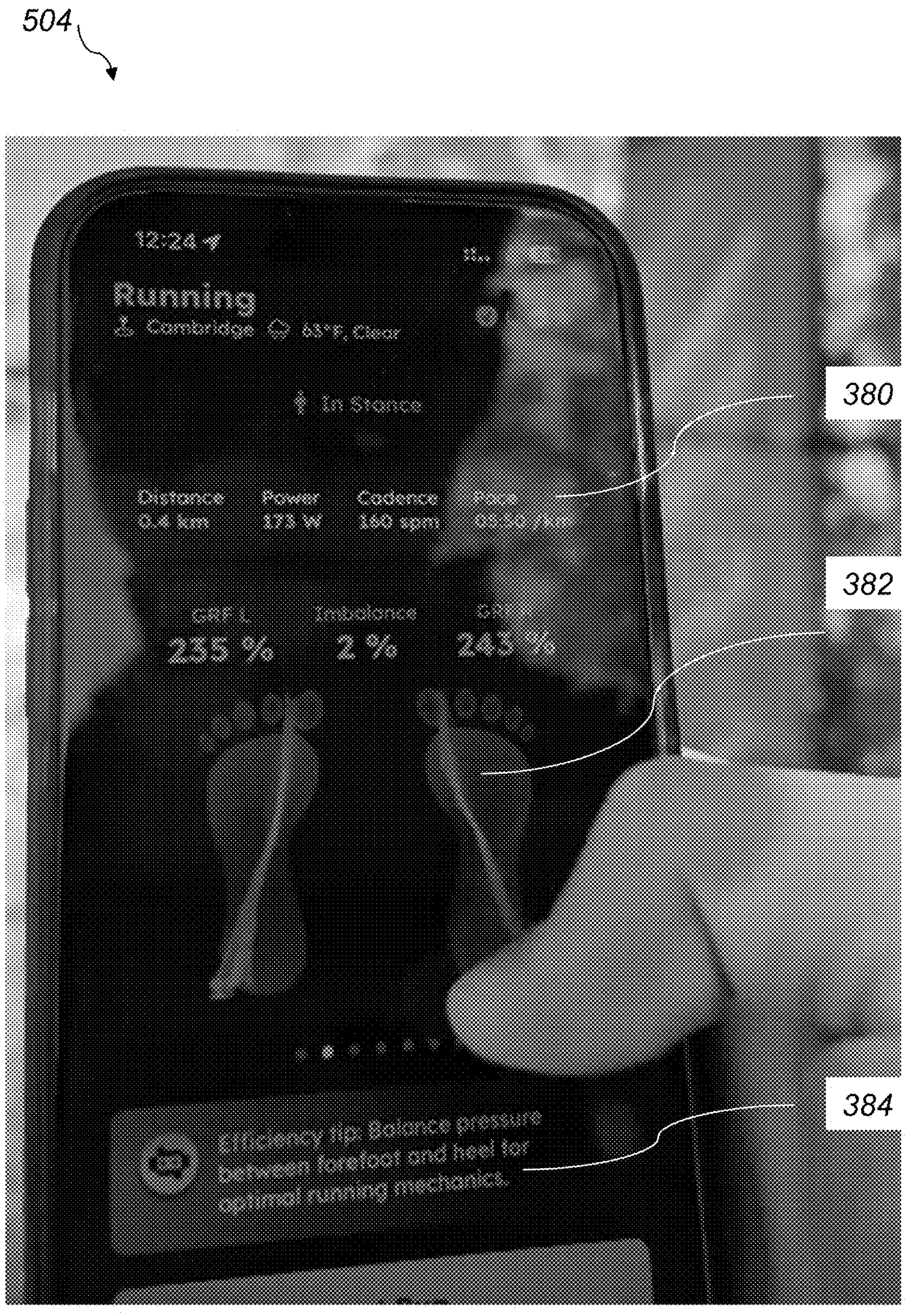
FIG. 11A shows a user interface (UI) of the AI application of FIG. 5A depicting pressure distribution data, as displayed in the user's phone.
Figure 11B:
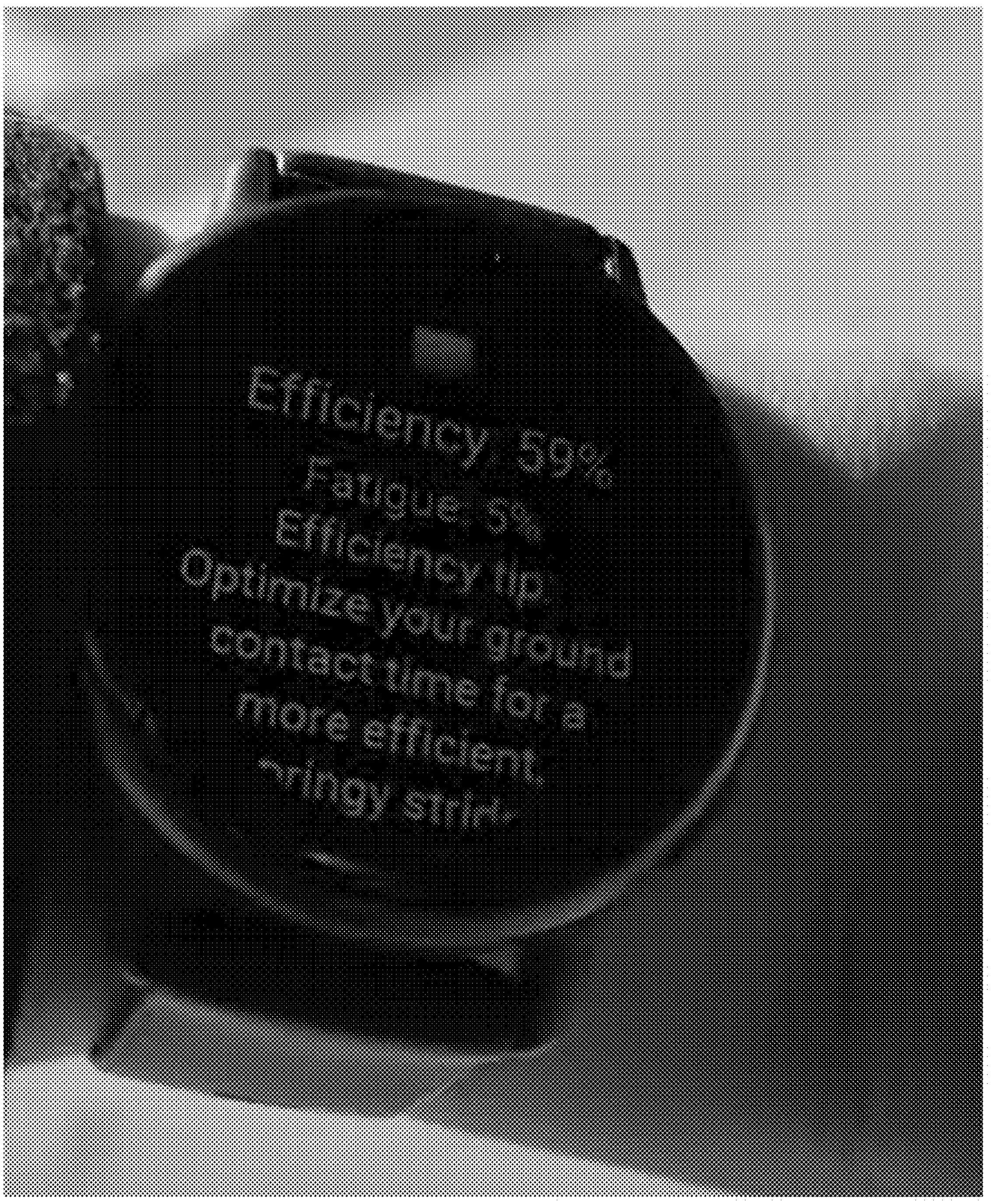
FIG. 11B shows a user interface of the AI application of FIG. 5A as displayed in the user's smart watch.
Figure 11C:
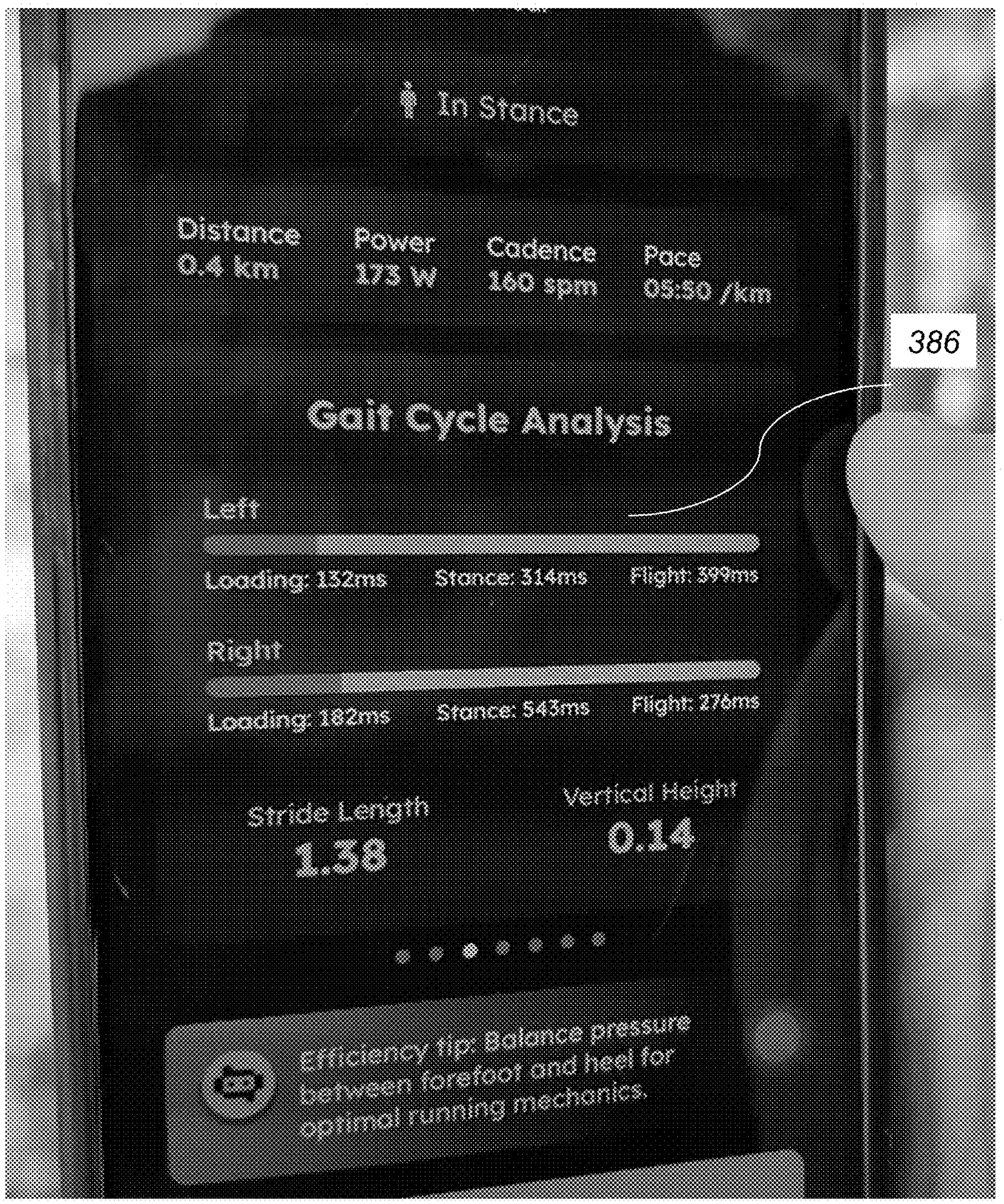
FIG. 11C shows the UI of FIG. 11A depicting gait analysis data.
Figure 11D:
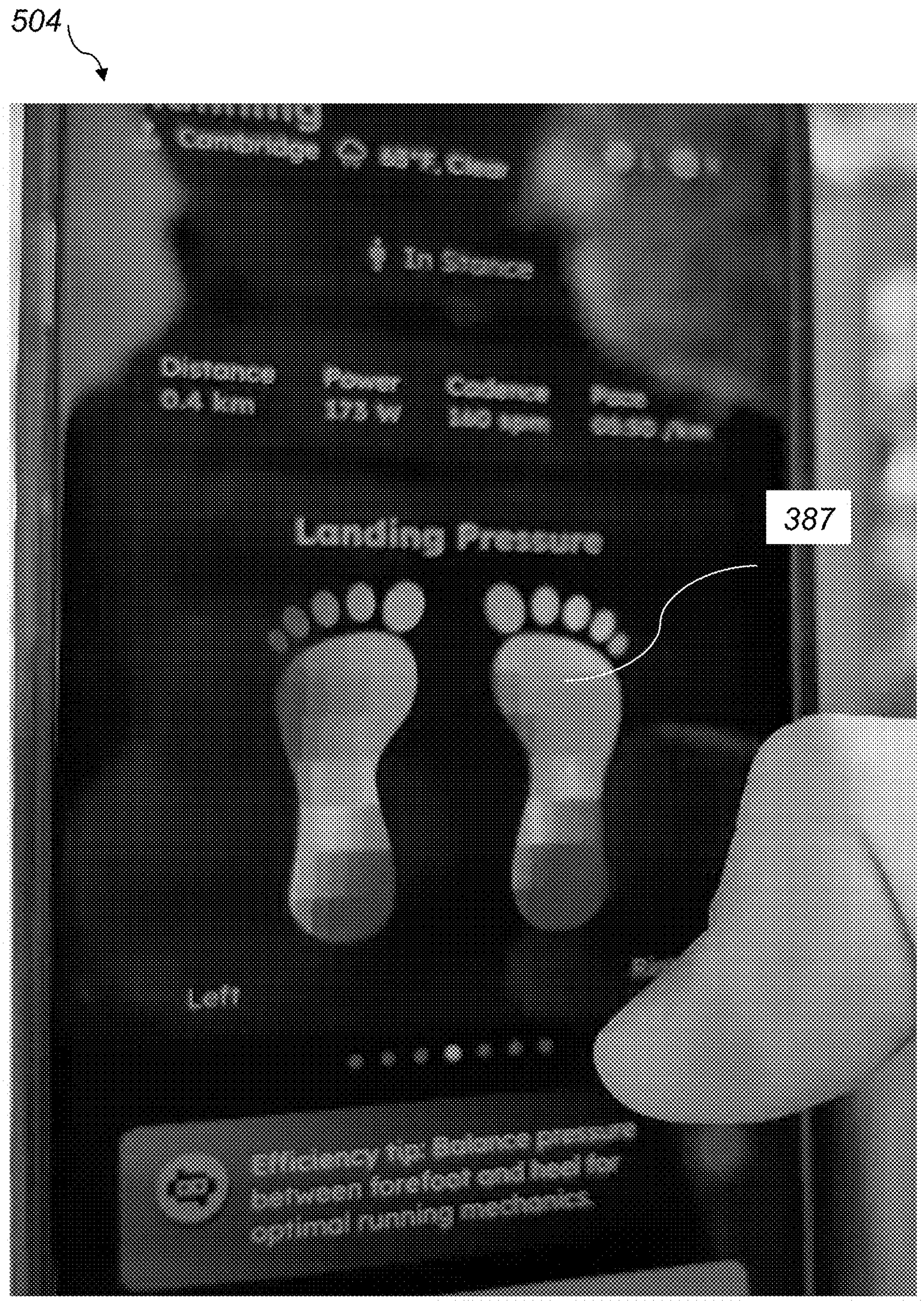
FIG. 11D shows the UI of FIG. 11A depicting landing pressure data.
Figure 11E:
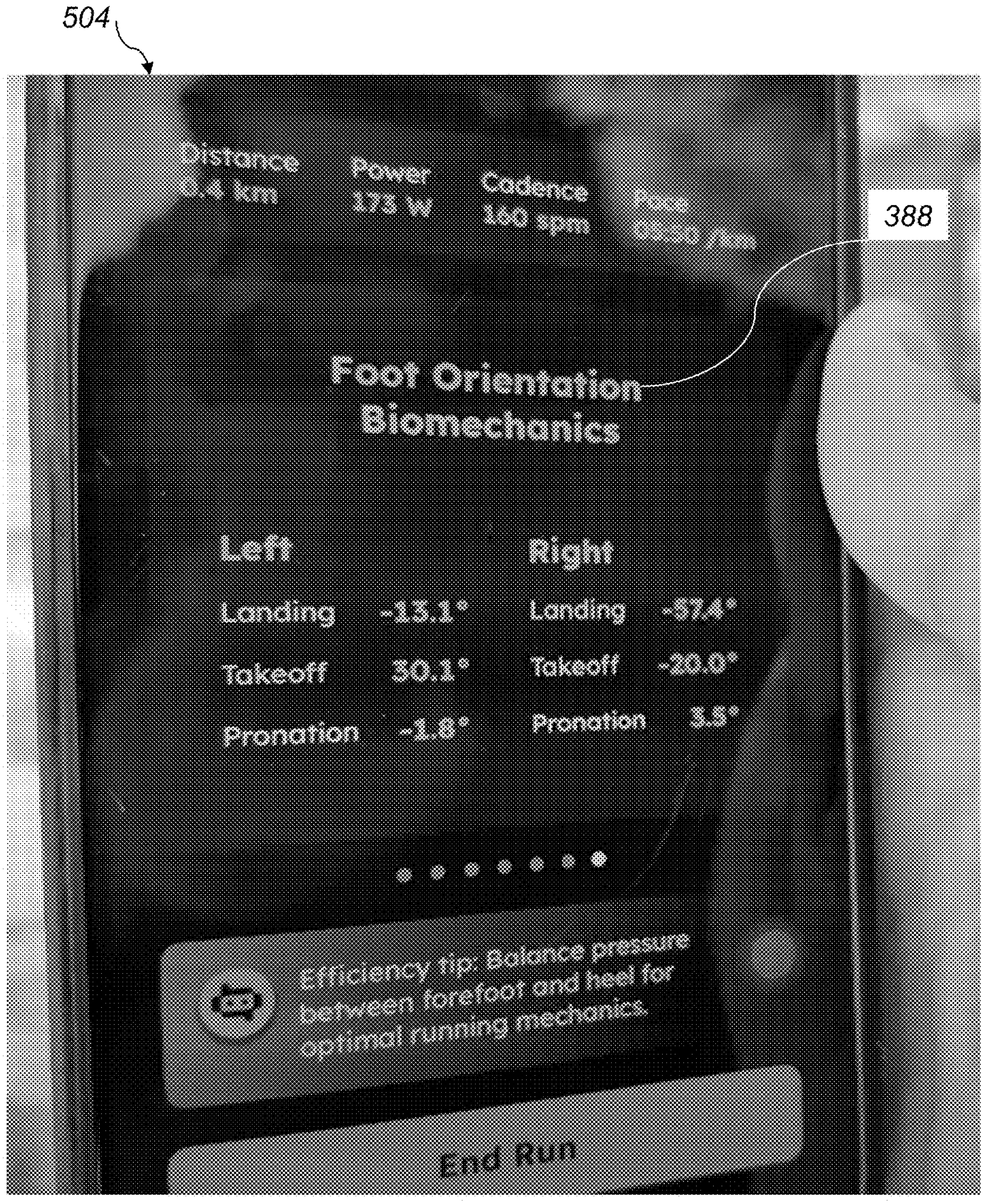
FIG. 11E shows the UI of FIG. 11A depicting foot orientation biomechanics data.
Figure 11F:
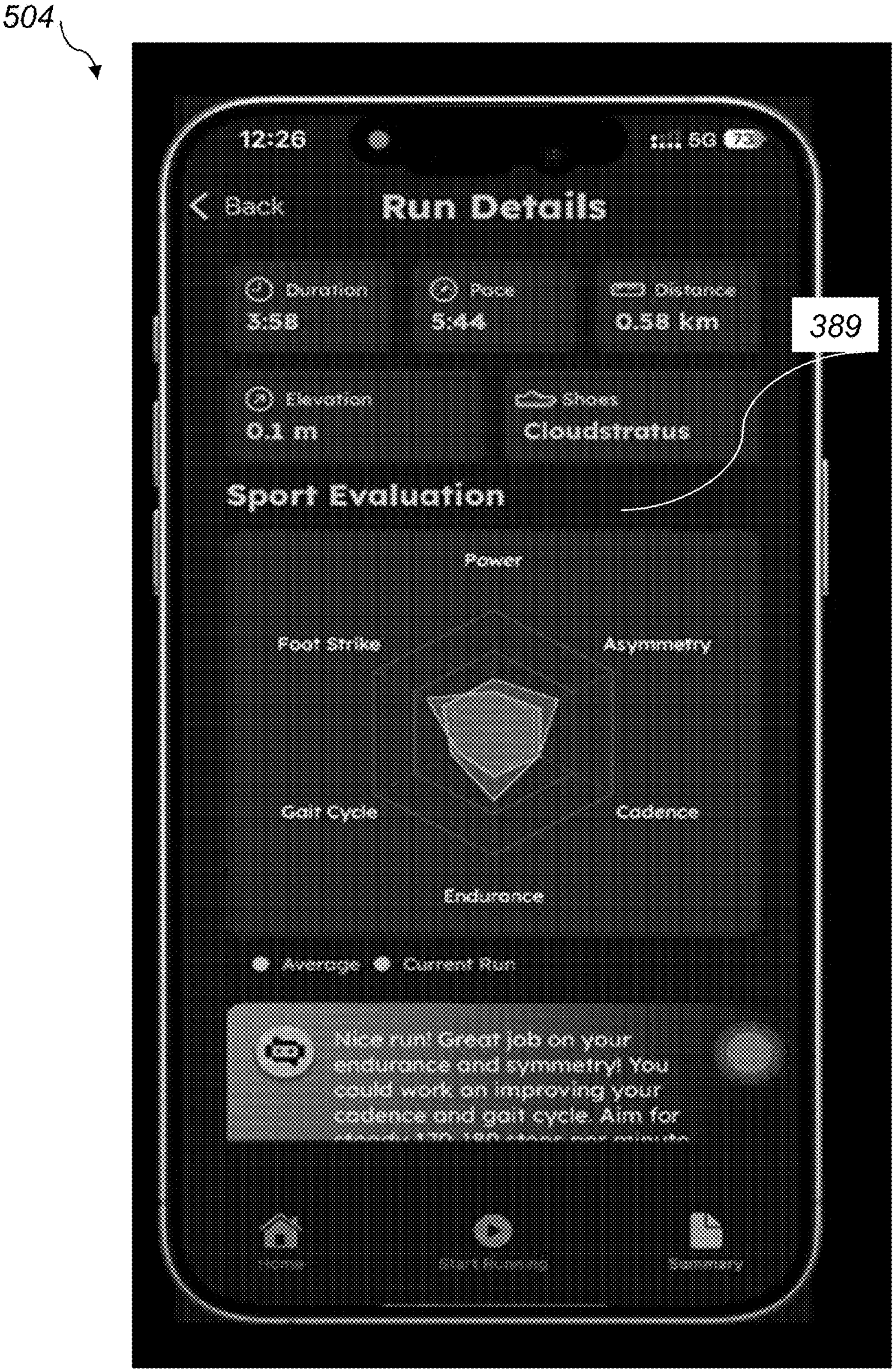
FIG. 11F shows the UI of FIG. 11A depicting run detail data.
Figure 11G:
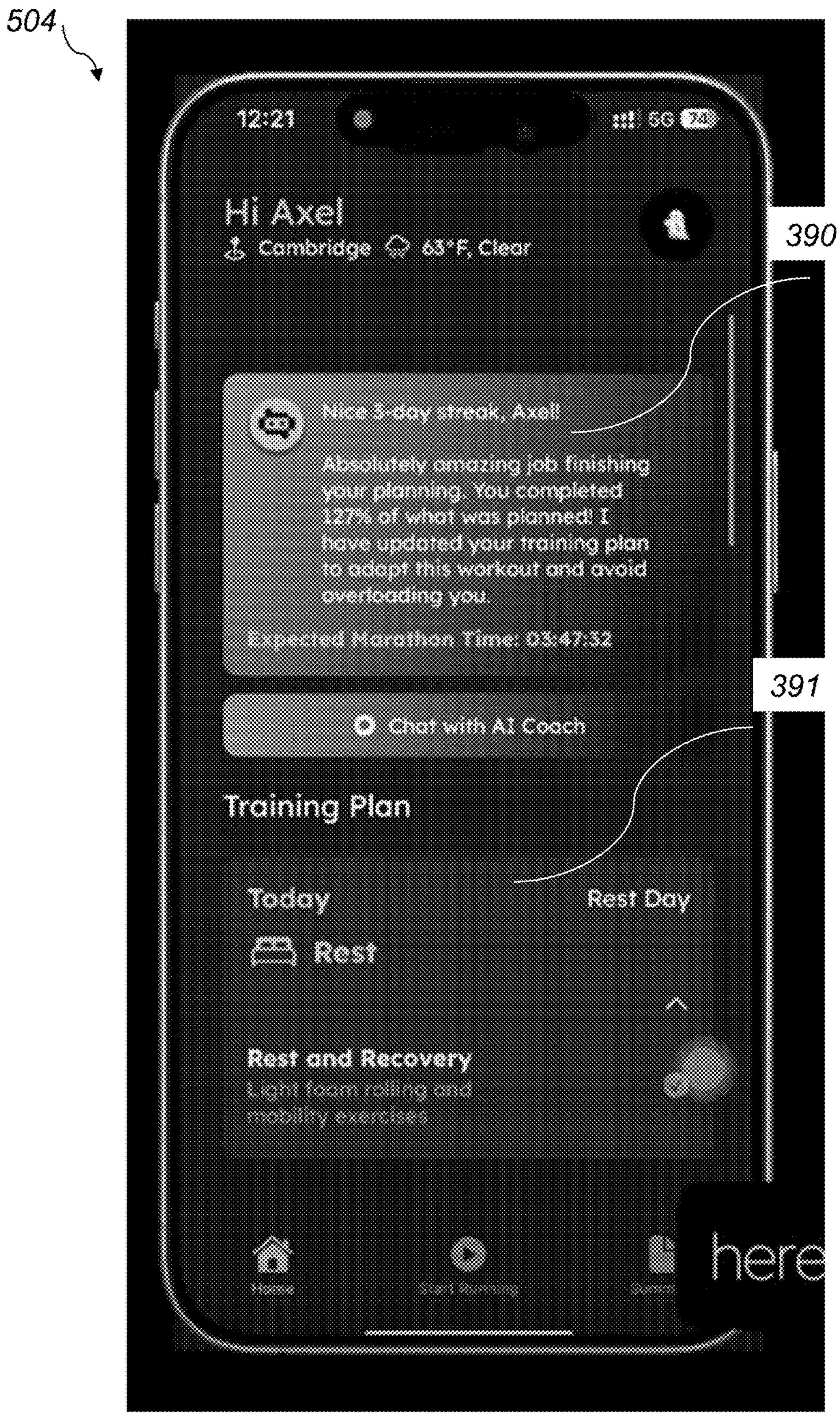
FIG. 11G shows the UI of FIG. 11A depicting a training summary and plan.

Examples of the generated data are shown in FIG. 11A-11G. FIG. 11A depicts running distance, power, cadence, pace, 380, and pressure distribution data for each foot 382, as shown in the user's phone 504. The pressure distribution data 382 depict the measured pressure distribution between forefoot and heel for each foot. The application 350 provides a running efficiency tip 384 by comparing the measured pressure distribution to a balanced pressure distribution. Similar data including efficiency, fatigue, and efficiency tips are also displayed in the user's watch 507, as shown in FIG. 11B. FIG. 11C depicts gait cycle analysis data for the left and right foot 386, stride length and vertical height. FIG. 11D depicts landing pressure data for the left and right foot 387. FIG. 11E depicts foot orientation biomechanics for the left and right foot 388. FIG. 11F depicts a summary of all run related data and an overall run evaluation 389. FIG. 111G depicts a summary of all run data up to a given time 390 and a training plan for the immediate future in order to reach a set goal 391.

This AI-driven process 350 emphasizes the smart shoe system's capability not just to collect and combine diverse data, but also to decode and articulate this information into actionable insights, pushing the boundaries of what is achievable in wearable health technology. The smart shoe system 100 pushes the boundaries of wearable technology by offering detailed insights into users' gait, biomechanical efficiency, hydration levels, and overall health metrics. This holistic solution not only integrates advanced sensor technologies with cutting-edge AI but also enhances user engagement through comparative analysis, gamification elements, and a comprehensive toolbox of support features. Users can connect with friends to motivate each other, participate in collaborative workouts, and engage in competitive challenges that make reaching health goals a fun and socially interactive experience. Additionally, the system provides tailored home-based exercises for injury rehabilitation and prevention, form improvement suggestions based on top athletes' data, and direct telehealth sessions with healthcare professionals. This integration of monitoring, support, and community interaction transforms personal health and performance monitoring, making the smart shoe system a pioneering leader in the next generation of personal health technology.

In another embodiment, the invention provides a method for enhancing user engagement and health management using the smart shoe system 500 of FIG. 4. AI application 300 is used to perform data analysis and to determine user engagement. As was mentioned above, system 500 collects biomechanical and physiological data from integrated sensors within the shoe insole and conductive socks, and uses a multi-modal AI model to process, analyze, and interpret the data. The system 500 also enable the users to connect with peers via a software platform to sync their performance data, facilitating comparative analysis that motivates and enhances user engagement through friendly competition and social interaction. System 500 also gamification and interactive feedback. In one example, system 500 implements gamification strategies within the software platform, including collaborative workouts and competitive fitness challenges, designed to engage users in health-promoting activities by making the attainment of fitness goals engaging and enjoyable. System 500 also provides real-time feedback to users based on their activity data, including personalized notifications and insights, which are displayed through a user-friendly interface to promote informed decision-making about health and fitness activities. System 500 also provides personalized health support and telehealth integration. In one example, system 500 provides tailored home-based exercise regimens that are automatically adjusted based on the user's progress, injury history, and current fitness level, specifically focusing on injury prevention and rehabilitation. System 500 also facilitate access to telehealth services directly through the platform, allowing users to schedule and conduct sessions with healthcare professionals who can provide personalized guidance based on the analyzed data from the smart shoe system. In summary, system 500 significantly advances the functionality of the smart shoe system 100, transforming it from a simple activity tracker to a comprehensive health management platform. It not only provides detailed insights into the user's physical activity and biomechanical efficiency, but also actively engages users in their health management through interactive features and personalized support. The integration of advanced sensor technology with sophisticated software analytics and user-centric functionalities exemplifies a novel approach in personal health and performance monitoring technology.

Real-World Applications

1. Real-World Applications of the Smart Insole System in Athletic Training

Setup and Calibration:

Before commencing training, athletes equip themselves with the smart shoe insole 110 and conductive socks 111 designed to interface seamlessly with their physiology and biomechanics. Using the mobile application 510, they connect the insoles 110 via Bluetooth to the mobile phone 504, ensuring stable and continuous data transmission. During this initial setup, athletes are prompted to input extensive baseline data including weight, age, typical activity levels, and previous injury history. This comprehensive calibration process tailors the system's sensors and algorithms to individual needs, enhancing the accuracy and relevance of the feedback provided (602), shown in FIG. 6.

Figure 6:
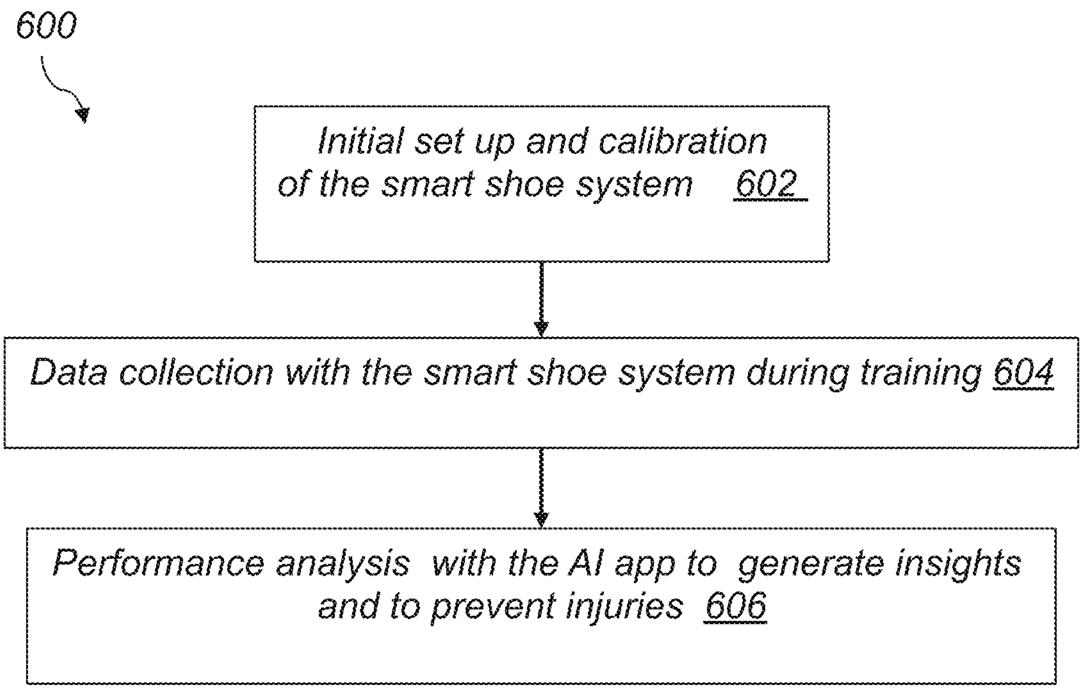
FIG. 6 is a flow diagram for the process of using the smart shoe system of FIG. 1B with the AI application of FIG. 5A for athletic training.

Training Sessions:

As athletes engage in their routines, the insole system gathers crucial data on foot force, timing, and orientation (604), shown in FIG. 6. It measures metrics such as peak ground reaction force, stride length, and foot strike angles. Additionally, by integrating bioimpedance sensors, the system can monitor changes in body composition and hydration levels, offering insights into muscle quality and fluid balance. This multifaceted approach allows for a detailed analysis of both kinesiology and physiological state, giving athletes a holistic view of their performance and physical condition.

Performance Analysis and Injury Prevention:

Post-exercise, the data collected offers a granular view of the athlete's performance, highlighting areas like gait asymmetry, potential biomechanical inefficiencies, and signs of muscle fatigue or imbalance. The system's advanced AI capabilities analyze patterns over time, identifying trends that may indicate emerging injury risks or areas for potential enhancement (606), shown in FIG. 6. For instance, shifts in bioimpedance measurements could suggest variations in muscle activation or recovery needs, prompting tailored advice for training adjustments or nutritional interventions.

This system not only propels athletes towards peak performance by offering precise, data-driven insights but also plays a critical role in injury prevention. By merging detailed biomechanical analysis with bioimpedance data, athletes receive a comprehensive understanding of their body's mechanics and internal state, enabling smarter training decisions and optimized recovery strategies. This level of integration fosters a cycle of continuous improvement, ensuring that training is both effective and aligned with the athlete's health and well-being.

2. Health Monitoring with the Smart Shoe System

Daily Wear:

Individuals aiming to maintain or enhance their health can seamlessly integrate the smart shoe system into their everyday life. Equipped with the insole and conductive socks, the shoes are worn during regular daily activities (612), shown in FIG. 7. This setup allows for the passive collection of valuable data on movement patterns, body composition, and other physiological metrics without disrupting the user's routine.

Figure 7:
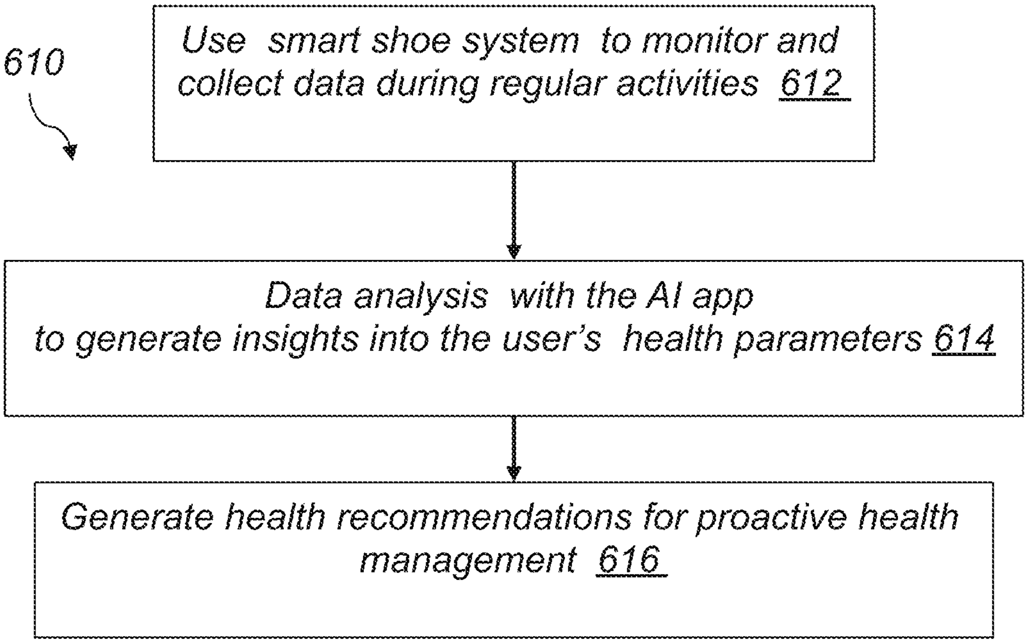
FIG. 7 is a flow diagram for the process of using the smart shoe system of FIG. 1B with the AI application of FIG. 5A for health monitoring.

Insight Generation:

The system leverages bioimpedance data along with recorded activity levels to generate insights into several critical health parameters (614), shown in FIG. 7. Users can gain an understanding of their hydration status, body fat percentage, and cardiovascular health. These insights are particularly valuable for assessing how daily lifestyle choices—such as activity levels, dietary intake, and fluid consumption—impact overall health.

Proactive Health Management:

Based on the data gathered, the system's application provides personalized recommendations aimed at enhancing the user's health (616), shown in FIG. 7. It might suggest strategies for better hydration, ideas for adjusting physical activity levels, or dietary changes to bolster cardiovascular health. This proactive approach to health management empowers users to make informed decisions that positively influence their long-term well-being, all guided by data-driven insights from their daily footwear.

3. Rehabilitation Support with the Smart Shoe System

Figure 8:
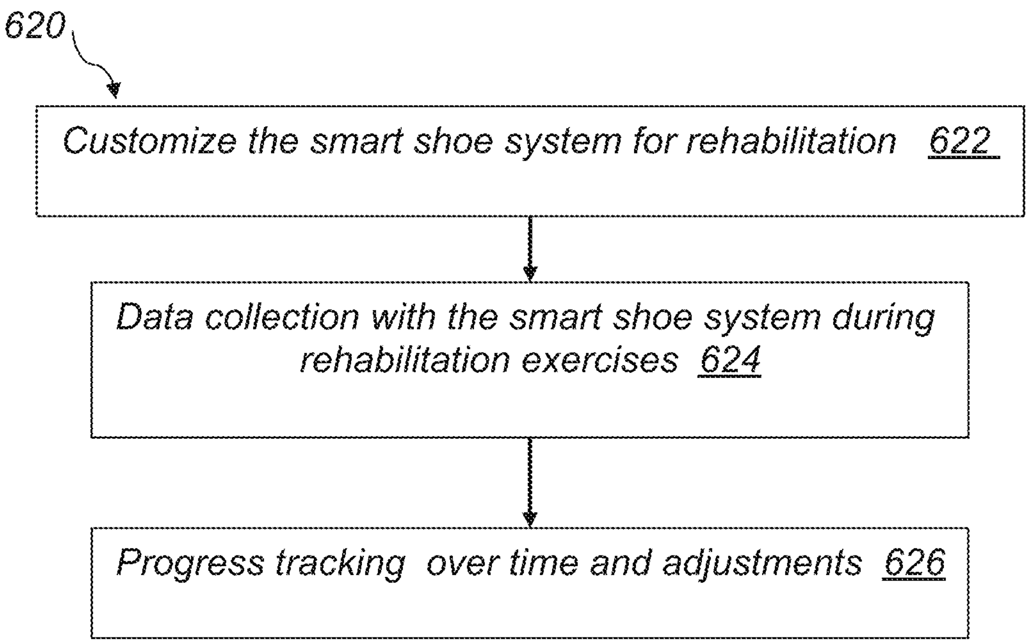
FIG. 8 is a flow diagram for the process of using the smart shoe system of FIG. 1B with the AI application of FIG. 5A for rehabilitation.

Rehabilitation Setup:

Users initiate their recovery by customizing the smart shoe system to their specific rehabilitation needs (622), shown in FIG. 8. Whether addressing common injuries like back pain or an ankle strain, the system is calibrated to the user's current mobility and strength. This setup incorporates plans for at-home exercises and offers optional telehealth support, providing a comprehensive approach to rehabilitation.

Recovery Monitoring:

As users engage in prescribed rehabilitation exercises, the system actively monitors their movements and provides real-time feedback (624), shown in FIG. 8. Incorporating bioimpedance technology, the system also assesses muscle and tissue health, tracking changes in tissue composition and hydration levels. This dual monitoring ensures that exercises are performed correctly and helps in managing tissue recovery, crucial for preventing further injury.

Progress Tracking and Adjustment:

The smart shoe system allows users to track their rehabilitation progress over time. (626), shown in FIG. 8. Bioimpedance data enriches this tracking by offering insights into muscle mass and edema, guiding the adjustment of exercise intensity and type based on the healing stage of the tissues. This tailored approach ensures that recovery exercises are safe and effectively matched to the user's evolving condition, facilitating a safe and efficient return to normal activity.

This versatile application of the smart shoe system not only enhances rehabilitation from injuries but also empowers users with detailed, data-driven insights into their recovery. By leveraging comprehensive physiological and biomechanical data, including bioimpedance analysis, the system supports informed decisions in rehabilitation and health management.

4. Chronic Condition Management with the Smart Shoe System

Figure 9:
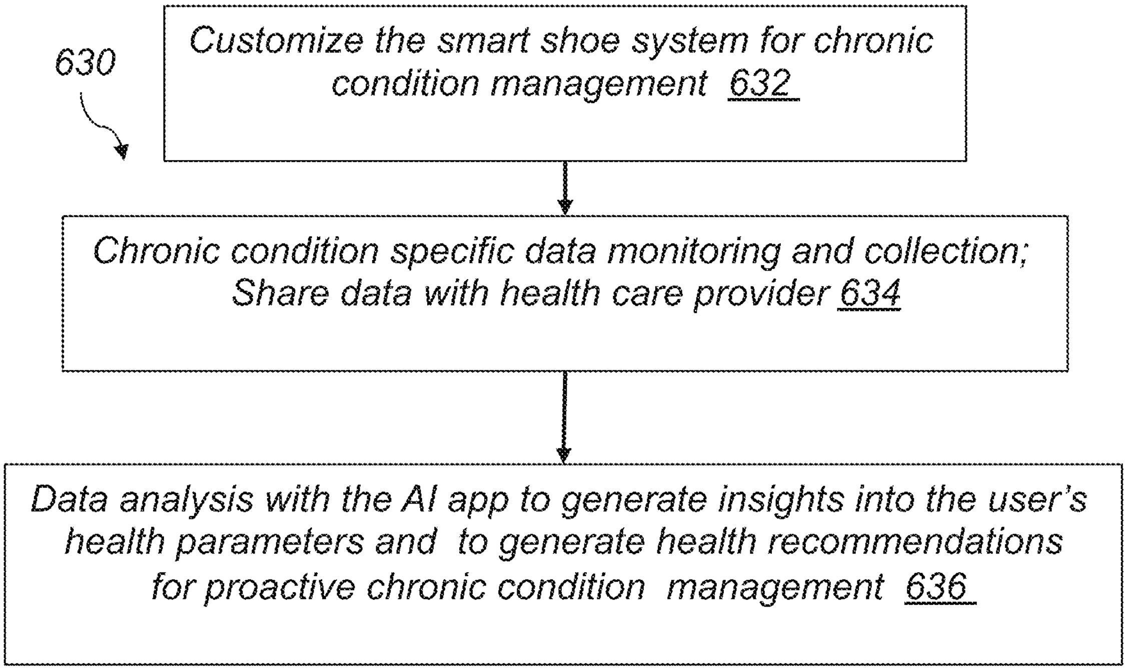
FIG. 9 is a flow diagram for the process of using the smart shoe system of FIG. 1B with the AI application of FIG. 5A for chronic condition monitoring.

Chronic Condition Setup:

For individuals managing chronic conditions like multiple sclerosis (MS), Parkinson's disease, or diabetes-related foot ulceration, the smart shoe system 100 is configured to monitor specific health indicators relevant to their conditions (632), shown in FIG. 9. This includes setting up personalized alerts and integrating telehealth capabilities, enabling seamless communication with healthcare providers.

Condition-Specific Monitoring:

The system continuously tracks the user's daily activities, providing insights into movement patterns and foot health that are crucial for managing these conditions (634), shown in FIG. 9:

- For MS and Parkinson's patients, monitoring helps detect changes in gait and balance, common issues that can indicate progression or fluctuation in condition severity. Real-time feedback assists in maintaining mobility and preventing falls.
- For diabetic patients with a risk of foot ulceration, the system tracks foot pressure distribution to identify areas of excessive pressure or friction that could lead to ulcers. Regular bioimpedance measurements also monitor tissue health and hydration, important for ulcer prevention and management.

Telehealth Integration and Proactive Management:

With integrated telehealth functionalities, patients can easily share their data with healthcare providers, facilitating proactive management of their conditions (636), shown in FIG. 9. Providers can review the collected data to:

- Adjust treatment plans based on quantifiable changes in the patient's condition, such as mobility reduction or signs of potential ulceration.
- Recommend modifications to physical therapy or medication in response to observed data trends, enhancing the effectiveness of interventions.
- Schedule remote consultations to discuss changes in condition, reducing the need for frequent in-person visits and enabling timely medical decisions.

This application of the smart shoe system provides individuals with chronic conditions a powerful tool to manage their health more effectively. By combining detailed biomechanical data with the capabilities of telehealth, the system empowers both users and healthcare providers to take a more active and informed role in chronic condition management, enhancing quality of life and health outcomes.

Figure 13:
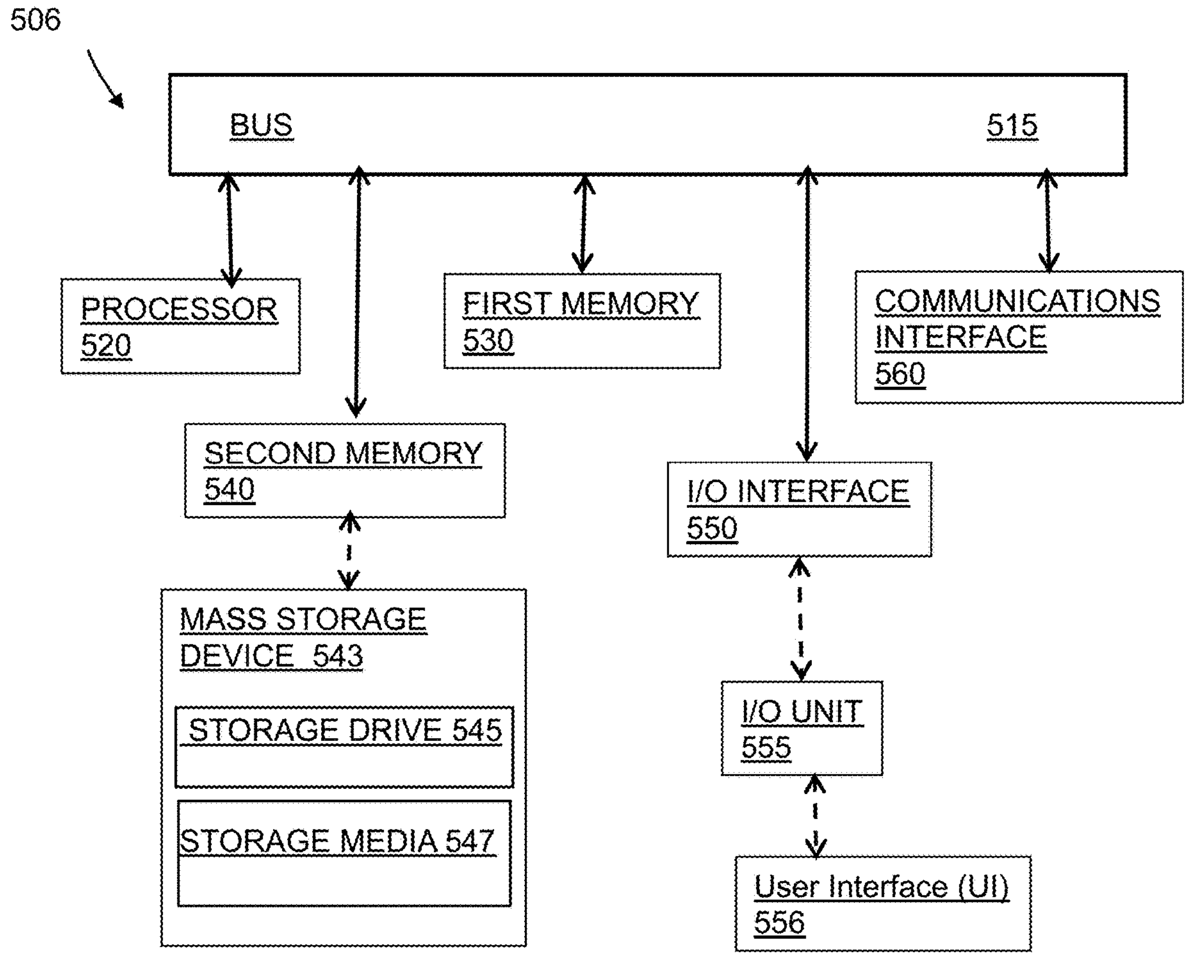
FIG. 13 is a schematic diagram of an exemplary computer system that is used to implement the system of the present invention.

Referring to FIG. 13, an exemplary computer system 506 or network architecture that may be used to implement the system of the present invention includes a processor 520, first memory 530, second memory 540, I/O interface 550 and communications interface 560. All these computer components are connected via a bus 515. One or more processors 520 may be used. Processor 520 may be a special-purpose or a general-purpose processor. As shown in FIG. 10, bus 515 connects the processor 520 to various other components of the computer system 506. Bus 515 may also connect processor 520 to other components (not shown) such as, sensors, and servomechanisms. Bus 515 may also connect the processor 520 to other computer systems. Processor 520 can receive computer code via the bus 515. The term "computer code" includes applications, programs, instructions, signals, and/or data, among others. Processor 520 executes the computer code and may further send the computer code via the bus 515 to other computer systems. One or more computer systems 506 may be used to carry out the computer executable instructions of this invention.

Computer system 506 may further include one or more memories, such as first memory 530 and second memory 540. First memory 530, second memory 540, or a combination thereof function as a computer usable storage medium to store and/or access computer code. The first memory 530 and second memory 540 may be random access memory (RAM), read-only memory (ROM), a mass storage device, or any combination thereof. As shown in FIG. 6, one embodiment of second memory 540 is a mass storage device 543. The mass storage device 543 includes storage drive 545 and storage media 547. Storage media 547 may or may not be removable from the storage drive 545. Mass storage devices 543 with storage media 547 that are removable, otherwise referred to as removable storage media, allow computer code to be transferred to and/or from the computer system 500. Mass storage device 543 may be a Compact Disc Read-Only Memory ("CDROM"), ZIP storage device, tape storage device, magnetic storage device, optical storage device, Micro-Electro-Mechanical Systems ("MEMS"), nanotechnological storage device, floppy storage device, hard disk device, USB drive, among others. Mass storage device 543 may also be program cartridges and cartridge interfaces, removable memory chips (such as an EPROM, or PROM) and associated sockets.

The computer system 506 may further include other means for computer code to be loaded into or removed from the computer system 506, such as the input/output ("I/O") interface 550 and/or communications interface 560. The computer system 506 may further include a user interface (UI) 556 designed to receive input from a user for specific parameters. Both the I/O interface 550 and the communications interface 560 and the user interface 556 allow computer code and user input to be transferred between the computer system 506 and external devices including other computer systems. This transfer may be bi-directional or omni-direction to or from the computer system 506. Computer code and user input transferred by the I/O interface 550 and the communications interface 560 and the UI 556 are typically in the form of signals, which may be electronic, electromagnetic, optical, or other signals capable of being sent and/or received by the interfaces. These signals may be transmitted via a variety of modes including wire or cable, fiber optics, a phone line, a cellular phone link, infrared ("IR"), and radio frequency ("RF") link, among others.

The I/O interface 550 may be any connection, wired or wireless, that allows the transfer of computer code. In one example, I/O interface 550 includes an analog or digital audio connection, digital video interface ("DVI"), video graphics adapter ("VGA"), musical instrument digital interface ("MIDI"), parallel connection, PS/2 connection, serial connection, universal serial bus connection ("USB"), IEEE1394 connection, PCMCIA slot and card, among others. In certain embodiments the I/O interface connects to an I/O unit 555 such as a user interface (UI) 556, monitor, speaker, printer, touch screen display, among others. Communications interface 560 may also be used to transfer computer code to computer system 506. Communication interfaces include a modem, network interface (such as an Ethernet card), wired or wireless systems (such as Wi-Fi, Bluetooth, and IR), local area networks, wide area networks, and intranets, among others.

Figure 12:
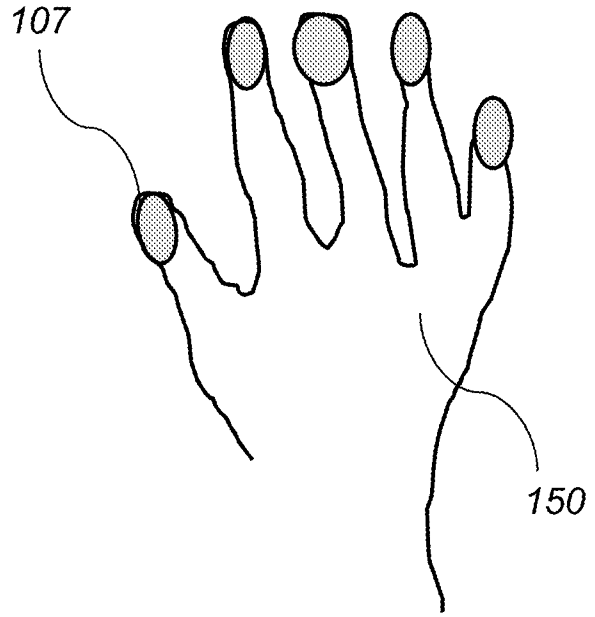
FIG. 12 depicts another application of the pressure system of FIG. 2A.

The invention is also directed to computer products, otherwise referred to as computer program products, to provide software that includes computer code to the computer system 506. Processor 520 executes the computer code in order to implement the methods of the present invention. In one example, the methods according to the present invention may be implemented using software that includes the computer code that is loaded into the computer system 500 using a memory 530, 540 such as the mass storage drive 543, or through an I/O interface 550, communications interface 560, user interface UI 556 or any other interface with the computer system 506. The computer code in conjunction with the computer system 506 may perform any one of, or any combination of, the steps of any of the methods presented herein. The methods according to the present invention may be also performed automatically, or may be invoked by some form of manual intervention. The computer system 506, or network architecture, of FIG. 12 is provided only for purposes of illustration, such that the present invention is not limited to this specific embodiment.

The smart shoe system described in this patent application represents a transformative advancement in wearable technology. It skillfully combines state-of-the-art sensor technology, advanced data processing techniques, and user-centric feedback mechanisms to deliver unprecedented insights into both biomechanical and physiological aspects of an individual's health. Incorporating textile-based pressure sensors, a versatile conductive sock system for precise bioimpedance analysis, and sophisticated capabilities for tracking motion and elevation changes, this system offers a comprehensive view of the wearer's physical status in real-time.

The invention detailed herein extensively covers not only the innovative manufacturing processes of these sensors but also their seamless integration into a unified system that excels in data fusion and insight generation. This smart shoe system not only showcases exemplary engineering and thoughtful design but also effectively fills a significant void in the market for integrated, real-time health and performance monitoring solutions.

By providing detailed analyses of the wearer's physical conditions and delivering actionable feedback directly to the user, the smart shoe system enables individuals to make well-informed decisions regarding their training routines, health management practices, and rehabilitation processes. As such, it sets a new benchmark in the wearable technology sector, paving the way for future innovations that continue to enhance the intersection of technology and personal health.

In other embodiments, the textile pressure sensor array 107 is used as a tactile sensor for robotic applications. In one example, five flexible, thumb-shaped pressure sensor modules 107 are used in the fingers of a robotic hand or a glove 150 to capture haptic signals in real time and a high frame rates, shown in FIG. 12. Each thumb-shaped pressure sensor module 107 includes more than twenty-five individual pressure sensing elements. These tactile sensor modules work together with a central processing unit (CPU) that quickly and accurately interprets the combined tactile data, thereby enabling precise and responsive control in dynamic robotic applications.

Several embodiments of the present invention have been described. Nevertheless, it will be understood that various modifications may be made without departing from the spirit and scope of the invention. Accordingly, other embodiments are within the scope of the following claims.

The invention claimed is:

1. A smart shoe system, comprising:

a shoe comprising a shoe body, a shoe sole, and an insole, wherein the shoe sole is attached to an outer surface of the shoe body's bottom, wherein the insole is located within the shoe body onto an inner surface of the shoe body's bottom, and wherein the shoe body is shaped and dimensioned to receive a user's foot;

a bioimpedance sensor system comprising impedance sensing electrodes, and an impedance sensing module;

wherein said insole comprises a flexible pressure sensor array;

wherein said flexible pressure sensor array comprises an upper electrode, a lower electrode, and a flexible composite piezoresistive layer interposed between the upper and lower electrodes; and wherein each of the upper and lower electrodes comprises a flexible substrate and a flexible conductive electrode structure that is bonded to said flexible substrate.

2. The smart shoe system of claim 1, further comprising a computing module electrically connected to said insole.

3. The smart shoe system of claim 2, wherein said computing module comprises an inertial measurement unit, a barometer, microcontroller, and a wireless signal transmitter.

4. The smart shoe system of claim 3, wherein said computing module further comprises said impedance sensing module and said computing module is electrically connected to said impedance sensing electrodes.

5. The smart shoe system of claim 4, further comprising a mobile communication device configured to wirelessly connect to the computing module via the wireless signal transmitter and to receive sensor data from said flexible pressure sensor array, said impedance sensing module, said inertial measurement unit, said barometer and said microcontroller.

6. The smart shoe system of claim 5, wherein said mobile communication device comprises an application that provides real time feedback to a user during use of said shoe based on said sensor data.

7. The smart shoe system of claim 5, wherein said sensor data are relayed to a computing cloud for advanced analysis by a computer and wherein said smart shoe system further comprises a cloud-based artificial intelligence (AI) application, which performs said advanced analysis of said sensor data by said computer.

8. The smart shoe system of claim 7, wherein said cloud-based artificial intelligence (AI) application comprises computation modules that perform said advanced analysis of said sensor data and wherein said computation modules comprise:

a first layer of encoders that encode said sensor data, and extract first feature data from all encoded sensor data;

a combinator that forms all possible combinations of said first feature data and generates combined first feature data;

a second layer of encoders that encode said combined first feature data and extract second feature data;

a data synthesis and analysis module that synthesizes and analyzes said first feature data and said second feature data and generates refined data;

a processor that processes said refined data and generates actionable insights into the user's physiological and biomechanical states; and wherein said first layer of encoders incorporates temporal sequences to said first feature data and creates a three-dimensional feature data space.

9. The smart shoe system of claim 5, wherein said mobile communication device comprises one of a mobile phone, a smart watch, a tablet, or a networked computing unit.

10. The smart shoe system of claim 2, further comprising a conductive sock comprising conductive fibers, and wherein the conductive sock surrounds the user's foot and is electrically connected to the computing module.

11. The smart shoe system of claim 2, wherein the computing module is located within the shoe sole, or is attached to the shoe sole's bottom.

12. The smart shoe system of claim 2, wherein the computing module is configured to be removably located onto the shoe body.

13. The smart shoe system of claim 1, wherein the flexible composite piezoresistive layer comprises an elastomer matrix impregnated with conductive particles.

14. The smart shoe system of claim 13, wherein the conductive particles comprise one of carbon black, graphene, graphene oxide, silver nanoparticles, carbon nanotubes (CNTs), copper nanoparticles, conductive polyaniline (PANI), Poly(3,4-ethylenedioxythiophene) polystyrene sulfonate (PEDOT:PSS), two-dimensional materials made of transition metal carbides, carbonitrides and nitrides (MXenes), metal-organic frameworks (MOFs), or combinations thereof.

15. The smart shoe system of claim 13, wherein said elastomer matrix comprises one of polyethylene (PE), low-density polyethylene (LDPE), polyurethane (PU), polydimethylsiloxane (PDMS), silicone rubber (VMQ), styrene-butadiene rubber (SBR), ethylene-vinyl acetate (EVA), fluoroelastomers (FKM), natural rubber (NR), or other flexible polymeric elastomers.

16. The smart shoe system of claim 1, the flexible composite piezoresistive layer comprises micro-dome elements and/or porous sections.

17. The smart shoe system of claim 1, wherein the flexible substrate comprises one of acetate, polyester, polyimide, or flexible polymer films.

18. The smart shoe system of claim 1, wherein the flexible conductive electrode structure comprises one of silver-plated fabrics, nickel/copper-plated fabric, conductive inks, or carbon-based conductive polymers.

19. The smart shoe system of claim 1, wherein the flexible conductive electrode structure is bonded to said flexible substrate via one of fabric glue, thermal bonding, ultrasonic welding, adhesive bonding or lamination techniques.

20. The smart shoe system of claim 1, wherein the flexible conductive electrode structure is shaped via laser cutting or high-precision die-cutting.

21. The smart shoe system of claim 1, wherein said insole further comprises a flexible printed circuit (FPC) and wherein the flexible pressure sensor array is connected to the FPC via a conductive adhesive.

* * * * *